(12) United States Patent
Gan et al.

(10) Patent No.: US 7,849,088 B2
(45) Date of Patent: Dec. 7, 2010

(54) REPRESENTATION AND EXTRACTION OF BICLUSTERS FROM DATA ARRAYS

(75) Inventors: Xiangchao Gan, Mang Zhang (CN); Alan Wee-Chung Liew, Tseung Kwan O (HK); Hong Yan, Glebe (AU)

(73) Assignee: City University of Hong Kong, Kowloon (HK)

( * ) Notice: Subject to any disclaimer, the term of this patent is extended or adjusted under 35 U.S.C. 154(b) by 197 days.

(21) Appl. No.: 11/461,152

(22) Filed: Jul. 31, 2006

(65) Prior Publication Data

US 2008/0027954 A1    Jan. 31, 2008

(51) Int. Cl.
G06F 7/00 (2006.01)
G06F 17/30 (2006.01)
G06F 15/16 (2006.01)

(52) U.S. Cl. .................. 707/737; 707/705; 707/736

(58) Field of Classification Search ...... 707/100–104.1, 707/2–6, 200, 1, 999.005, 999.006, 737, 707/999.001–9, 999.102, 999.104, 999.107; 706/15–20

See application file for complete search history.

(56) References Cited

U.S. PATENT DOCUMENTS

| | | | | |
|---|---|---|---|---|
| 6,289,354 | B1 * | 9/2001 | Aggarwal et al. | 707/104.1 |
| 7,035,739 | B2 * | 4/2006 | Schadt et al. | 702/19 |
| 7,075,547 | B2 * | 7/2006 | Moon | 345/581 |
| 7,406,212 | B2 * | 7/2008 | Mohamed et al. | 382/281 |
| 7,567,972 | B2 * | 7/2009 | Geiselhart et al. | 1/1 |
| 2005/0278324 | A1 * | 12/2005 | Fan et al. | 707/6 |
| 2006/0184459 | A1 * | 8/2006 | Parida | 706/1 |
| 2008/0021897 | A1 * | 1/2008 | Lepre | 707/6 |

OTHER PUBLICATIONS

Madeira, S.C. and Oliveira, A. L., "Biclustering algorithms for biological data analysis: A survey," IEEE Transactions on Computational Biology Bioinformatics, Jan.-Mar. 2004, vol. 1, pp. 24-45.*

Li, H., Lavin, M. A., and Le Master, R. J., "Fast Hough Transform: A Hierarchical Approach," Computer Vision, Graphics, and Image Processing, 1986, vol. 36, pp. 139-161.*

Li, H., Lavin, M.A., and Le master, R. J., "Fast Hough Transform: A hierarchical Approach," Computer Vision, Graphics, and Image Processing, 1986, vol. 36, pp. 139-161.*

Rakesh Agrawal, Johannes Gehrke, Dimitrios Gunopolos, Prabhakar Raghavan, "Automatic Subspace Clustering of High Demensional Data for Data Mining Applications", IBM Almaken Research Center, 650 Harry Rioad, San Jose, CA 95120, vol. 27, Issue 2 (Jun. 1998).*

Tavazoie, S., et al., "Systematic determination of genetic network architecture," Nature Genetics, vol. 22, 1999, pp. 281-285.

(Continued)

Primary Examiner—Cam Y Truong
Assistant Examiner—Cecile Vo
(74) Attorney, Agent, or Firm—Heslin Rothenberg Farley & Mesiti P.C.

(57) ABSTRACT

Gene expression, or other data is analyzed for the presence of biclusters. The data is represented as geometric data. Lines, planes and/or hyperplanes are detected in the geometric data using a transform such as a Hough Transform or its variations. The detected lines, planes and hyperplanes are analyzed to determine if they correspond to biclusters in the original data.

24 Claims, 16 Drawing Sheets

OTHER PUBLICATIONS

Eisen, M.B., et al., "Cluster analysis and display of genome-wide expression patterns," Proc. Natl. Acad. Sci. USA, 1998, vol. 95, pp. 14863-14868.

Tamayo, P., et al., "Interpreting patterns of gene expression with self-organizing maps: Methods and application to hematopoietic differentiation," Proc. Natl. Acad. Sci. USA, 1999, vol. 96, pp. 2907-2912.

Segal, E., et al., "Rich probabilistic models for gene expression," Bioinformatics, vol. 17, 2001, pp. 243-252.

Kluger, Y., Basri, R., Chang, J. T., and Gerstein, M., "Spectral Biclustering of Microarray Data: Coclustering Genes and Samples," Genome Research, Cold Spring Harbor Laboratory Press ISSN 1088-9051/03, 2003, vol. 13, 703-716.

Li, H., Lavin, M. A., and Le Master, R. J., "Fast Hough Transform: A Hierarchical Approach," Computer Vision, Graphics, and Image Processing, 1986, vol. 36, pp. 139-161.

Kiryati, N., Eldar,Y., and Bruckstein, A.M., "A Probabilistic Hough Transform," Pattern Recognition, 1990, vol. 24, pp. 303-316.

Xu, L. and Oja, E., "Rnadomized Hough Transform (RHT): Basic Mechanisms, Algorithms, and Computational Complexities," CVGIP: Image Understanding, vol. 57, No. 2, Mar. 1993, pp. 131-154.

Gan, X., Liew, A. W. C., and Yan, H, "Microarray missing data imputation based on a set theoretic framework and biological knowledge," Nucleic Acids Research, 2006, vol. 34, No. 5, pp. 1608-1619.

Tanay, A., Sharan, R. and Shamir, R., "Discovering statistically significant biclusters in gene expression data," Bioinformatics, vol. 18, Suppl. 1, 2002, pp. S136-S144.

Delong, M., et al., "DIG—a system for gene annotation and functional discovery," Bioinformatics, vol. 21, No. 13, 2005, pp. 2957-2959.

Ashburner, M., et al., "Gene Ontology: tool for the unification of biology," The Gene Ontology Consortium, Nature Genetics, 2000, vol. 25, pp. 25-29.

* cited by examiner

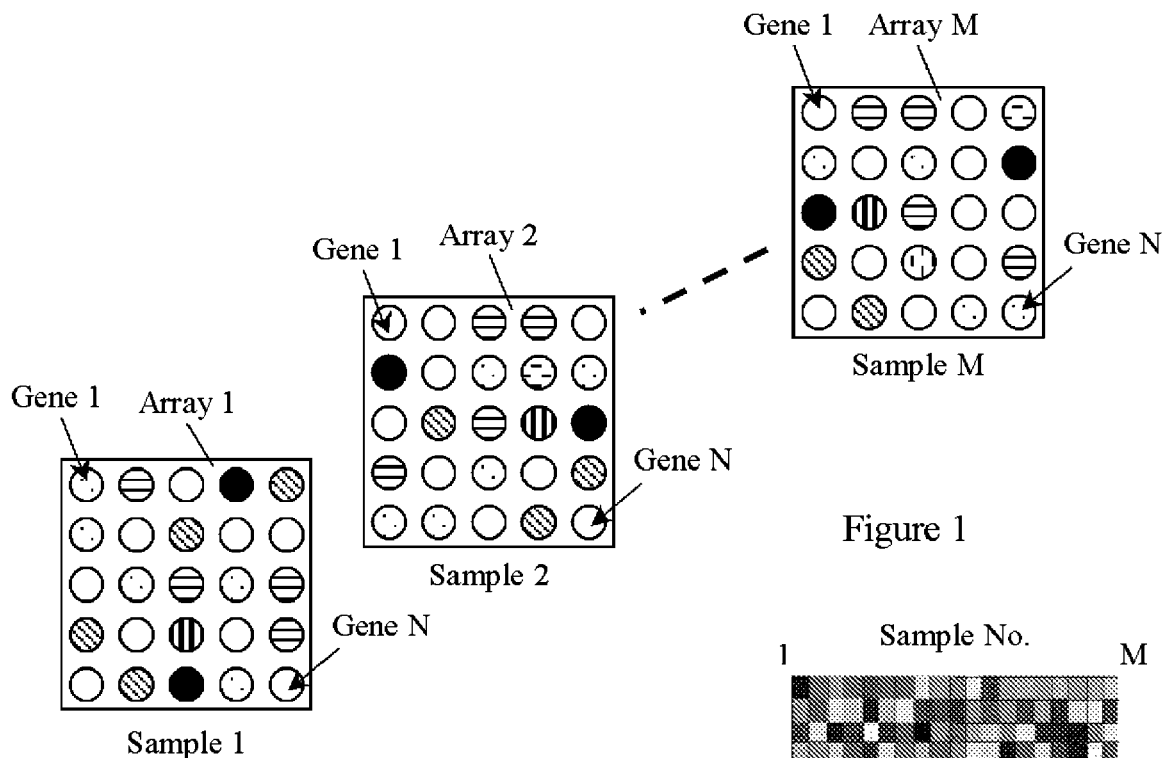
Figure 1
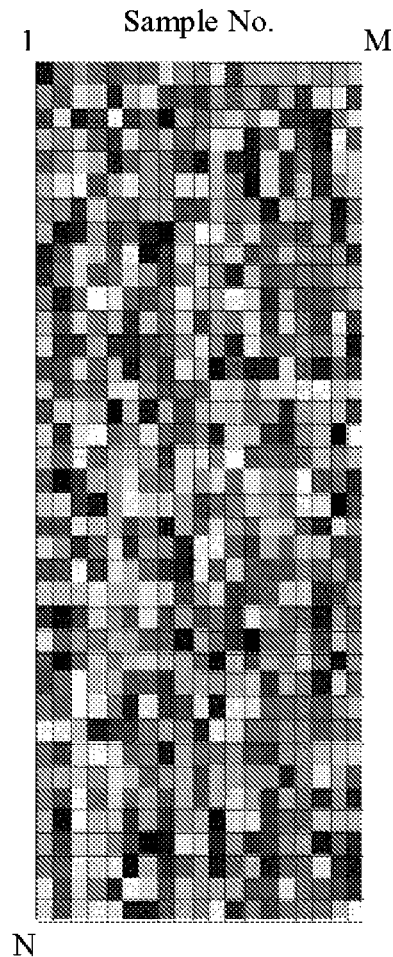
Figure 2(a)
Figure 2(b)

| x | y | z | w |
|---|---|---|---|
| 1.2 | 1.2 | 1.2 | 1.2 |
| 1.2 | 1.2 | 1.2 | 1.2 |
| 1.2 | 1.2 | 1.2 | 1.2 |
| 1.2 | 1.2 | 1.2 | 1.2 |
Figure 3(a)
| x | y | z | w |
|---|---|---|---|
| 1.2 | 1.2 | 1.2 | 1.2 |
| 2.0 | 2.0 | 2.0 | 2.0 |
| 1.5 | 1.5 | 1.5 | 1.5 |
| 3.0 | 3.0 | 3.0 | 3.0 |
Figure 3(b)
| x | y | z | w |
|---|---|---|---|
| 1.2 | 2.0 | 1.5 | 3.0 |
| 1.2 | 2.0 | 1.5 | 3.0 |
| 1.2 | 2.0 | 1.5 | 3.0 |
| 1.2 | 2.0 | 1.5 | 3.0 |
Figure 3(c)
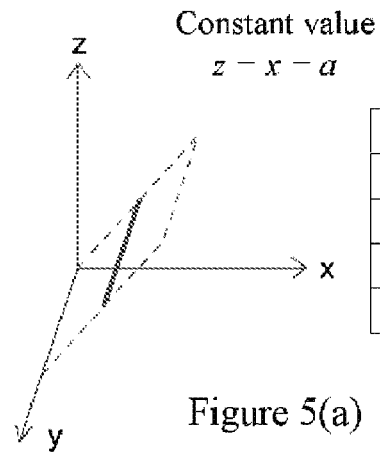
| x | y | z |
|---|---|---|
| 1.2 | 5 | 1.2 |
| 1.2 | 9 | 1.2 |
| 1.2 | 4 | 1.2 |
| 1.2 | 0 | 1.2 |
Figure 5(a)
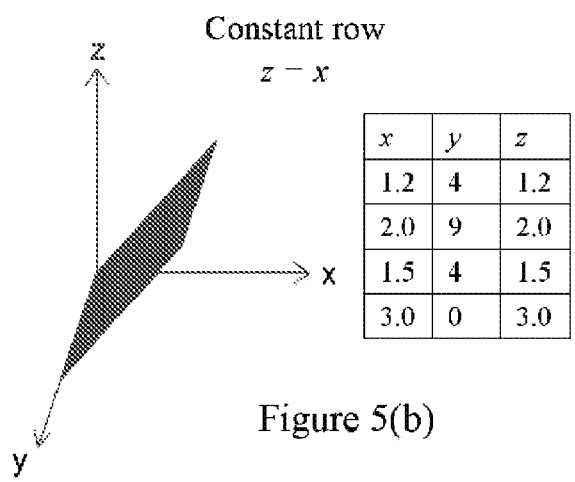
| x | y | z |
|---|---|---|
| 1.2 | 4 | 1.2 |
| 2.0 | 9 | 2.0 |
| 1.5 | 4 | 1.5 |
| 3.0 | 0 | 3.0 |
Figure 5(b)
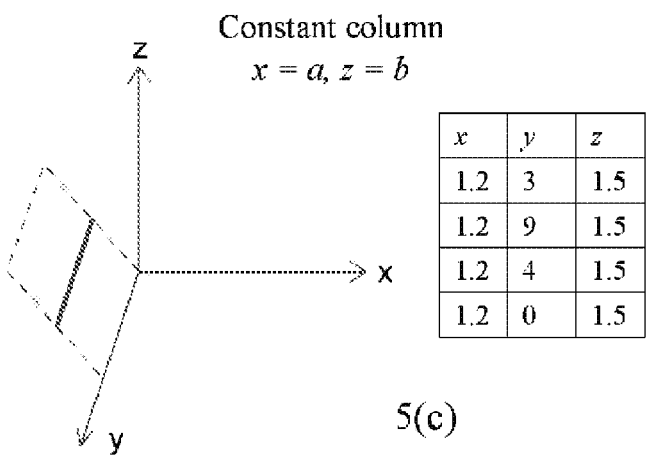
| x | y | z |
|---|---|---|
| 1.2 | 3 | 1.5 |
| 1.2 | 9 | 1.5 |
| 1.2 | 4 | 1.5 |
| 1.2 | 0 | 1.5 |
5(c)

| x | Y | z | w |
|---|---|---|---|
| 1.2 | 2.2 | 0.2 | 3.2 |
| 2.0 | 3.0 | 1.0 | 4.0 |
| 1.4 | 2.4 | 0.4 | 3.4 |
| 2.4 | 3.4 | 1.4 | 4.4 |
Figure 3(d)
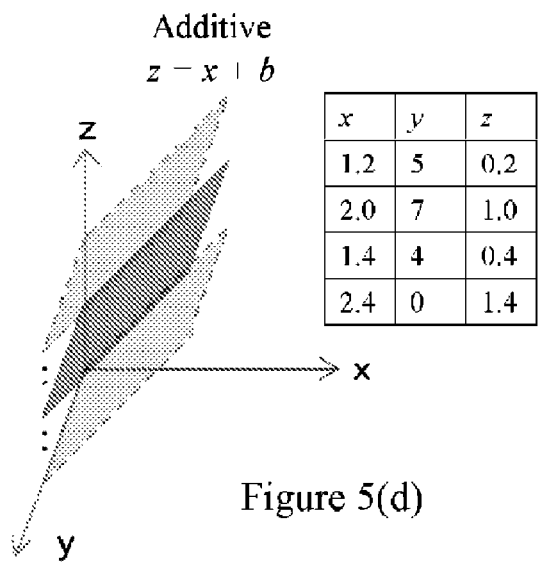
Figure 5(d)
| x | y | z | w |
|---|---|---|---|
| 1.0 | 2.0 | 0.5 | 1.5 |
| 2.0 | 4.0 | 1.0 | 3.0 |
| 1.4 | 2.8 | 0.7 | 2.1 |
| 2.4 | 4.8 | 1.2 | 3.6 |
Figure 3(e)
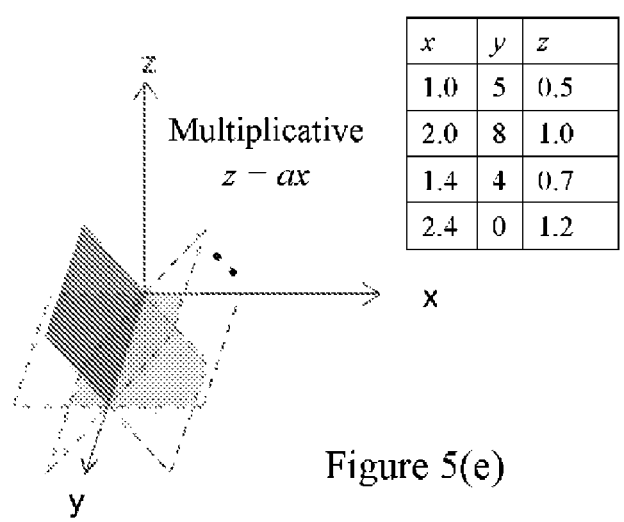
Figure 5(e)
| x | y | z | w |
|---|---|---|---|
| 1.0 | 2.1 | 0.6 | 1.7 |
| 2.0 | 4.1 | 1.1 | 3.2 |
| 1.4 | 2.9 | 0.8 | 2.3 |
| 2.4 | 4.9 | 1.3 | 3.8 |
Figure 3(f)
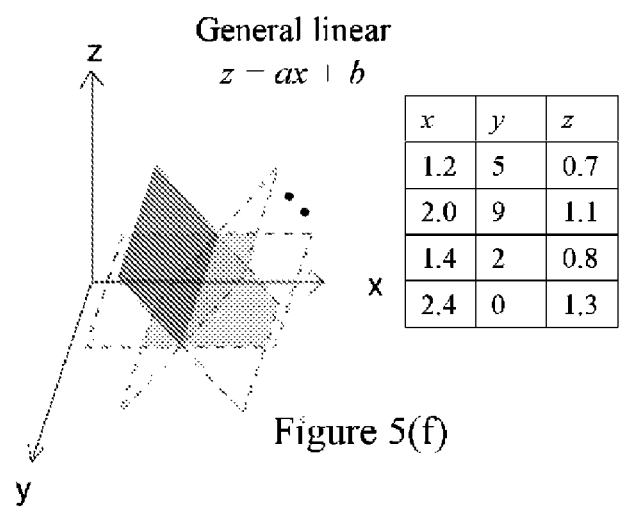
Figure 5(f)

REPRESENTATION AND EXTRACTION OF BICLUSTERS FROM DATA ARRAYS

FIELD OF THE INVENTION

The present invention relates to the representation and extraction of biclusters in data, using a geometrical method, in particular using hyperplane detection, for instance by way of the Hough Transform (including its variations). It is useful in data mining from many types of data, including, but not limited to, financial data, and particularly useful in gene expression data, for example from microarrays.

BACKGROUND

The use of computers in the modern world has provided people with an excess of data. Spotting patterns and trends in this data is important if much use is to be made of that data. It is also made difficult by the very quantity of data to be analyzed. Seeking such useful information amongst the data is often referred to as data mining and it is performed usefully in such disparate areas as biotechnology (e.g. DNA experiments), chemical reaction and chemical process development and the finance industry (e.g. consumer spending, foreign exchange rates, and stock market data).

The present invention was particularly developed with microarray data analysis in mind, but is also applicable in searching for patterns in other types of data.

In DNA experiments, a number of genes are exposed to a series of experimental conditions or to one set of experimental conditions over a length of time, with gene expression data derived for each experimental condition or time. FIG. 1 schematically shows a typical approach which is to use M different microarrays Array 1, Array 2, . . . , Array M, each of the same set of N genes, each microarray representing the set of gene expression data for a particular experimental condition 1, 2, . . . , M, time period $t_1, t_2, \ldots, t_M$, or other condition. These different conditions give rise to different samples 1 to M.

Results from sets of microarrays are often provided in N×M data matrices of standardized expression levels, for instance as shown in FIG. 2(a). The rows represent the results for the individual genes and the columns the results for the individual samples. The standardized expression level $e_{ij}$ is the standardized expression level of gene i of sample j.

The standardized expression levels are determined from the actual expression levels in the samples by any one of a number of known ways, e.g. using the ratio of the data with the expression level for the same gene in a control or using the log of such ratios, using the ratio of the data to the sum of the data and the expression level for the same gene in a control, using the difference between data and the expression level for the same gene in a control, or any of a number of other known methods. In the examples presented herein, the standardization that has been used is:

$$e_{ij} = \log \frac{\overline{R}_{ij}^{feature} - \overline{R}_{ij}^{background}}{\overline{G}_{ij}^{feature} - \overline{G}_{ij}^{background}},$$

where:

$\overline{R}_{ij}^{feature}$ and $\overline{G}_{ij}^{feature}$ are, respectively, the average red (cy5 dyes) and green (cy3 dyes) intensity levels of the data at point ij in a number of nominally identical and identically processed arrays;

$\overline{R}_{ij}^{background}$ and $\overline{G}_{ij}^{background}$ are, respectively, the average red (cy5 dyes) and green (cy3 dyes) intensity levels at the same point ij computed from a background area or from a number of nominally identical and identically processed control arrays after the same processing;

The expression level matrix of FIG. 2(a) is often converted into a visual array, of varying levels of red (for larger $e_{ij}$) and green (for smaller $e_{ij}$) and mixtures thereof. A black and white print out of such an array is shown in FIG. 2(b).

A key step in the analysis of gene expression data is to discover groups of genes that share similar transcriptional characteristics. Clustering gene expression data into homogeneous groups is instrumental in functional annotation, tissue classification and motif identification. However, standard clustering methods, such as:

k-means (for instance as described in Tavazoie S, Hughes J D, Campbell M J, Cho R J, Church G M: Systematic determination of genetic network architecture. Nat Genet 1999, 22:281-285);

hierarchical clustering algorithms (for instance as described in Eisen M B, Spellman P T, Brown P O, Botstein D: Cluster analysis and display of genome-wide expression patterns. Proc Natl Acad Sci USA 1998, 95:14863-14868); and self-organizing maps (for instance as described in Tamayo P, Slonim D, Mesirov J, Zhu Q, Kitareewan S, Dmitrovsky E, Lander E S, Golub T R: Interpreting patterns of gene expression with self-organizing maps: methods and application to hematopoietic differentiation. Proc Natl Acad Sci USA 1999, 96:2907-2912), have their limitations: they require that the related genes behave similarly across all measured samples. However, in many situations, an interesting cellular process is active only in a subset of the samples, or a single gene may participate in multiple pathways that may or may not be co-active under all samples. Also, when the data to be analyzed include many heterogeneous samples from many experiments, a clustering algorithm often cannot produce a satisfactory solution. To overcome such difficulties, biclustering is often used.

In gene expression data, a bicluster is a subset of genes exhibiting a consistent pattern over a subset of samples [Cheng, Y. and Church, G. M. (2000) Biclustering of expression data. Proceedings of the Eighth International Conference on Intelligent Systems for Molecular Biology (ISMB), 93-103]. This means that biclustering performs clustering in the row and column dimensions simultaneously (when applied to a matrix such as expression level matrix of FIG. 2(a)). There are a number of different bicluster patterns that are useful for gene expression data analysis, such as constant values, constant rows or columns and coherent values.

Most existing biclustering algorithms work by making permutations of the data matrix and detecting sub-matrices within the data matrix, such that a merit function is optimized. A comprehensive survey [in Madeira, S. C., and Oliveira, A. L. (2004) Biclustering algorithms for biological data analysis: a survey. IEEE/ACM Trans. Computational Biology Bioinformatics, 1, 24-45] points out that different biclustering algorithms iteratively search for the best possible subgrouping of the data using data mining techniques. The general strategy in all these algorithms can be described as adding or deleting rows and/or columns in the data matrix in some optimal ways such that an appropriate merit function is improved by the action.

The above-mentioned Madeira and Oliveira review of recent literature on biclustering indicates that there are several classes of biclusters. Three major classes of these are:

(i) biclusters with constant values;
(ii) biclusters with constant values in rows or columns; and
(iii) biclusters with coherent values in rows or columns.

FIGS. 3(a) to 3(f) show several different types of biclusters:

FIG. 3(a) constant bicluster;

FIG. 3(b) constant rows;

FIG. 3(c) constant columns;

FIG. 3(d) coherent values with additive model, where each row or column can be obtained by adding a constant to another row or column;

FIG. 3(e) coherent values with multiplicative model, where each row or column can be obtained by multiplying another row or column by a constant value; and FIG. 3(f) coherent values on columns with linear model, where each column can be obtained by multiplying another column by a constant value and then adding a constant.

The pattern in FIG. 3(f) is most general here and all other patterns, of FIGS. 3(a) to 3(e) can be regarded as special cases of this general pattern.

The Madeira and Oliveira review classified existing biclustering algorithms according to specific patterns the algorithms can detect. For example, the Double Conjugated Clustering (DCC) and block clustering algorithms are designed to detect constant values (FIG. 3(a)). The Coupled Two-Way Clustering (CTWC) and Gibbs algorithm focus on biclusters of the constant rows or columns (FIG. 3(b) or 3(c)). Segal, E., Taskar, B., Gasch, A., Friedman, N. and Koller, D. (2001) Rich probabilistic models for gene expression. Bioinformatics, 17, 243-252, assumes the additive model (FIG. 3(d)) in its algorithm and Kluger, Y., Basri, R., Chang, J. T., and Gerstein, M. (2003) Spectral biclustering of microarray data: co-clustering genes and samples. Genome Research, 13, 703-716, develops an algorithm for the multiplicative model (FIG. 3(e)).

In these methods, the type of patterns to be detected depends on the merit function used. Although it is possible to transform a bicluster of different type (i.e., constant rows) into a reference type (such as constant values bicluster), the necessary transformation is not known a priori for that bicluster. Determination of the appropriate transformation is further complicated by the presence of noise in the data.

SUMMARY OF THE INVENTION

An aim of the present invention is to provide improvements in various aspects of data analysis by bicluster detection. The invention provides an approach to data analysis using geometrical methods, such as detecting bicluster patterns using a generic line or plane finding algorithm. The invention is particularly useful in gene expression data analysis.

The gene expression data is represented as geometric data. Lines, planes and/or hyperplanes are detected in the geometric data using a transform such as a Hough Transform or its variations. The detected lines, planes and hyperplanes are analyzed to determine if they correspond to biclusters in the original gene expression data.

The present invention presents a novel interpretation of the biclustering problem in terms of the spatial distribution of data points in geometrical data space.

According to a first aspect of the present invention, there is provided a method for use in analyzing data, in particular gene expression data, for biclusters. Treating the data as geometric data, hyperplanes are detected in the data. Those hyperplanes may then be analyzed to see if they correspond to biclusters. The method comprises detecting hyperplanes in the data, the hyperplanes having at least two dimensions and obeying an equation $$F_M = \sum_{i=1}^{M-1} \beta_i F_i + \beta_M,$$

wherein $\{F_1, F_2, \ldots, F_M\}$ are co-ordinates of points in the data and $\{\beta_1, \beta_2, \ldots, \beta_M\}$ are parameters, and M corresponds to a number of dimensions in the data. The method further comprises determining whether the hyperplanes represent biclusters in the data, and outputting the determined biclusters, the detecting hyperplanes in the data comprising transforming the data into parameter space by applying a transform to the data.

According to another aspect of the present invention, there is provided apparatus for use in analyzing data, in particular gene expression data, for biclusters. The apparatus for analyzing data for biclusters comprises a processor in communication with a memory storing instructions for execution by the processor to perform a method. The method comprises transforming the data into parameter space by applying a transform to the data, detecting hyperplanes in the transformed data, the hyperplanes having at least two dimensions and obeying an equation $$F_M = \sum_{i=1}^{M-1} \beta_i F_i + \beta_M,$$

wherein $\{F_1, F_2, \ldots, F_M\}$ are co-ordinates of points in the data and $\{\beta_1, \beta_2, \ldots, \beta_M\}$ are parameters and M corresponds to the number of dimensions in the data, and determining whether the detected hyperplanes represent biclusters in the data. Typically, the apparatus will be a computer. However, it may be otherwise and include dedicated or programmable circuitry for detecting the hyperplanes.

Another aspect of the invention comprises a computer program product. This embodies a program of executable instructions to effect a method for use in analyzing data, in particular gene expression data, for biclusters. The instructions include at least individual or groups of modules for detecting hyperplanes having at least two dimensions in said gene expression data as if it were geometric data. The product may be software on a memory, whether a portable memory or on a remote memory accessible via a network.

In the present invention, the biclustering problem is changed from the identification of coherent sub-matrices in the data matrix to that of detecting structures of known geometry (lines or planes), particularly in high dimensional data space. This approach opens up the possibility of performing biclustering using generic line or plane finding algorithms, in particular those which provide a unified formulation and an efficient technique for extracting different types of biclusters simultaneously. There are many such algorithms that can be used, not just those exemplified or mentioned herein.

The present invention can provide an interpretation of the biclustering problem in terms of the geometric distributions of data points in the high dimensional data space. In this perspective, the biclustering problem can be considered to be that of detecting structures of known geometry, i.e., hyperplanes, in the high dimensional data space. Many common types of bicluster can be reduced to different spatial arrangements of the hyperplanes in the high dimensional data space. On this basis biclustering can be performed geometrically using hyperplane detection algorithms.

Based on this approach, in a preferred embodiment, a biclustering algorithm is provided for gene expression data using the well known Hough transform. A coarse-to-fine mechanism can be used to overcome the effect of noise in the data and to speed up the computation. Biclustering of various patterns on data sets, with anything from only one embedded bicluster to multiple overlapping biclusters can be performed. The results indicate that the preferred algorithm can detect all biclusters successfully.

INTRODUCTION TO THE DRAWINGS

The present invention may be further understood from the following description of non-limitative examples, with reference to the accompanying description, in which:

FIG. 1 is a schematic view of a prior art set of microarray samples;

FIG. 2(a) is a prior art N×M data matrix of standardized expression levels, from a set of microarray samples;

FIG. 2(b) is a prior art N×M visual matrix corresponding to the data matrix of FIG. 2(a);

Figure 4:
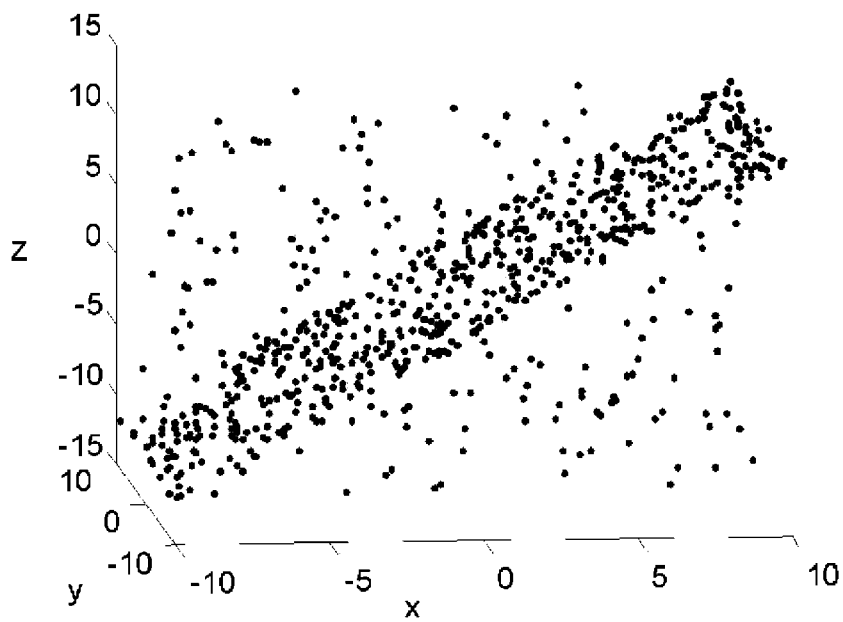
Figure 6:
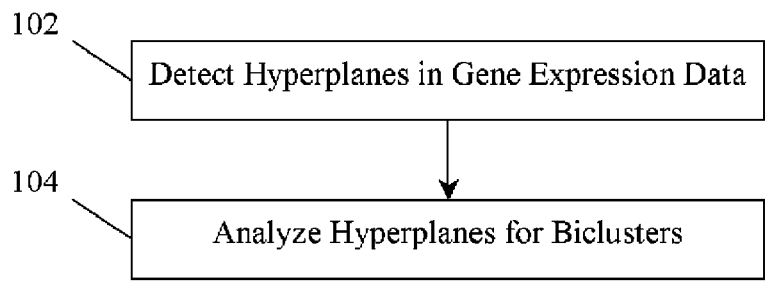
Figure 7:
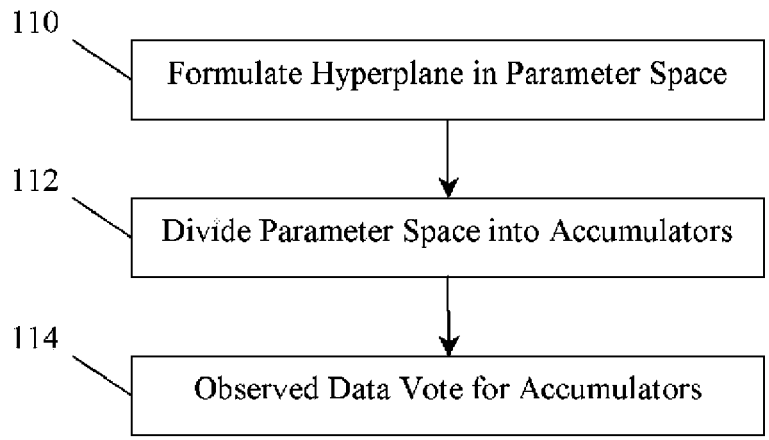
Figure 8:
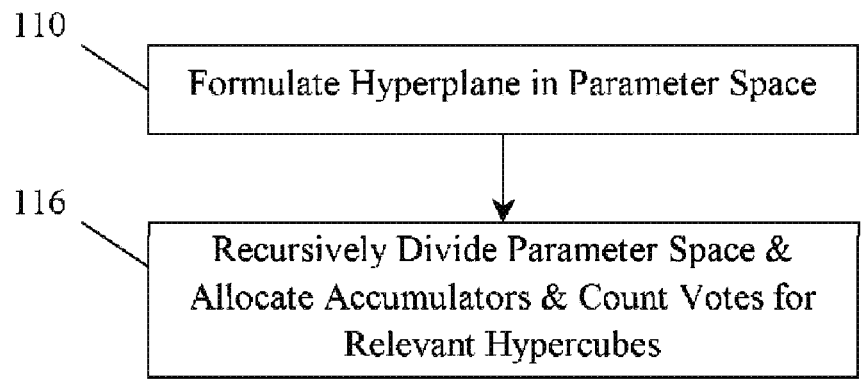
Figure 10:
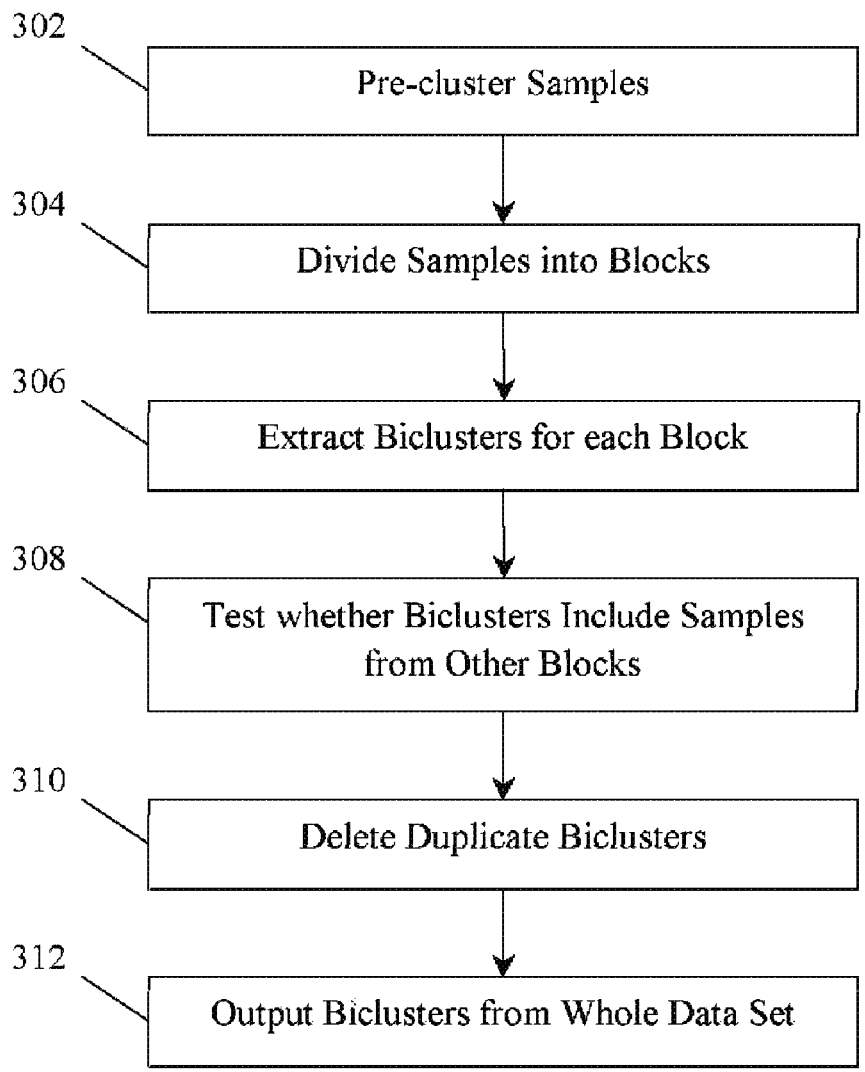
Figure 9:
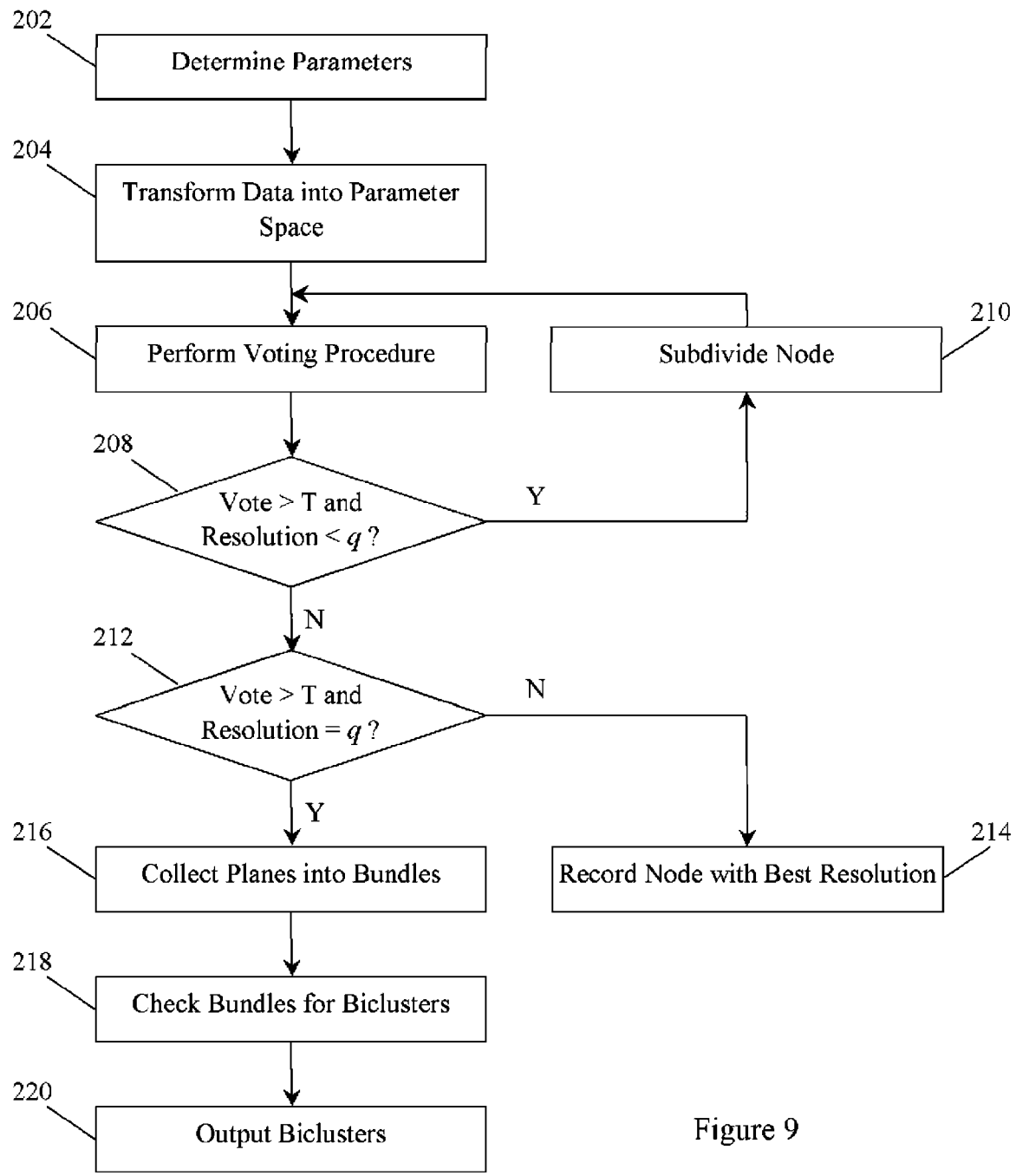
Figure 11:
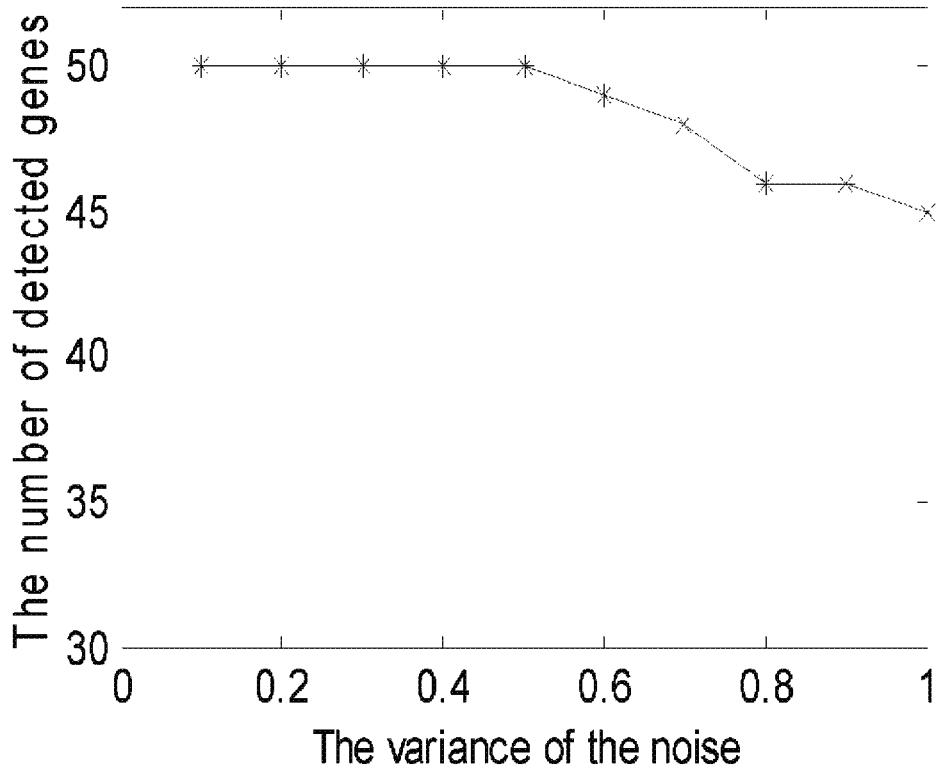
Figure 14F:
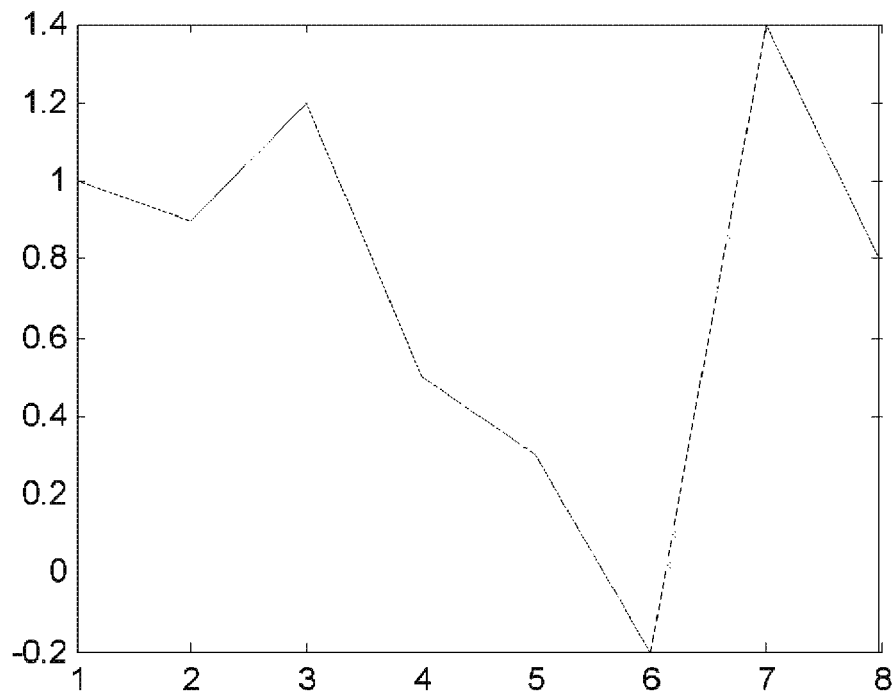
Figure 12A:
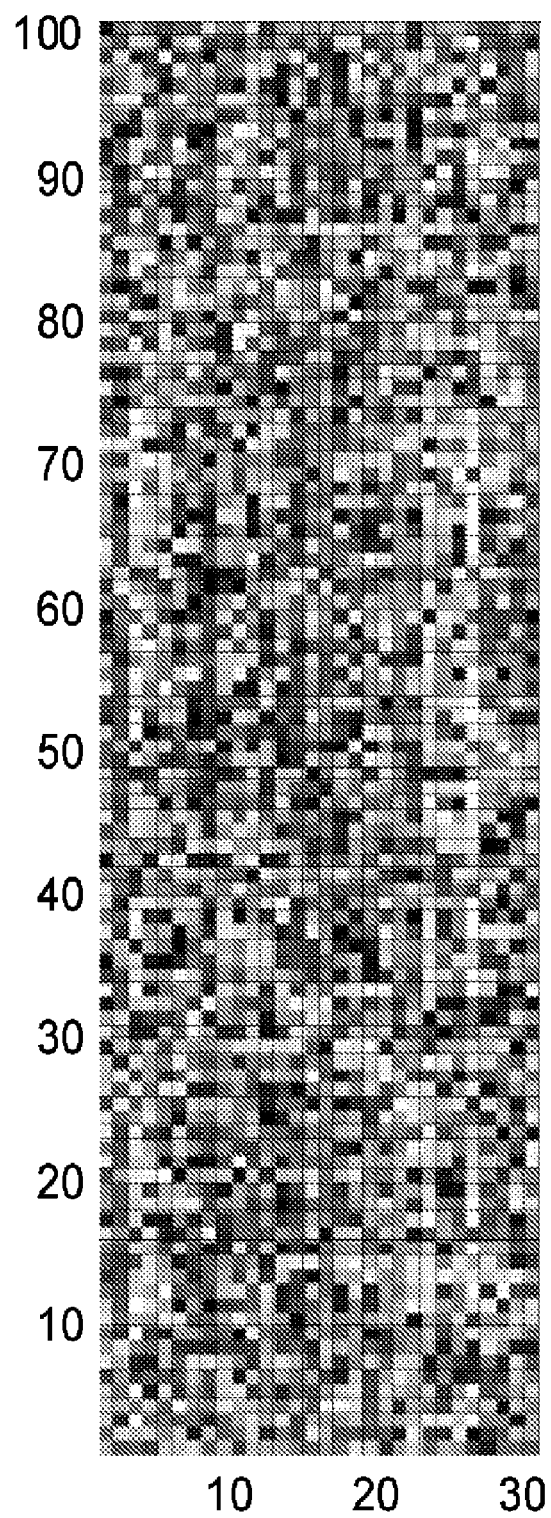
Figure 12B:
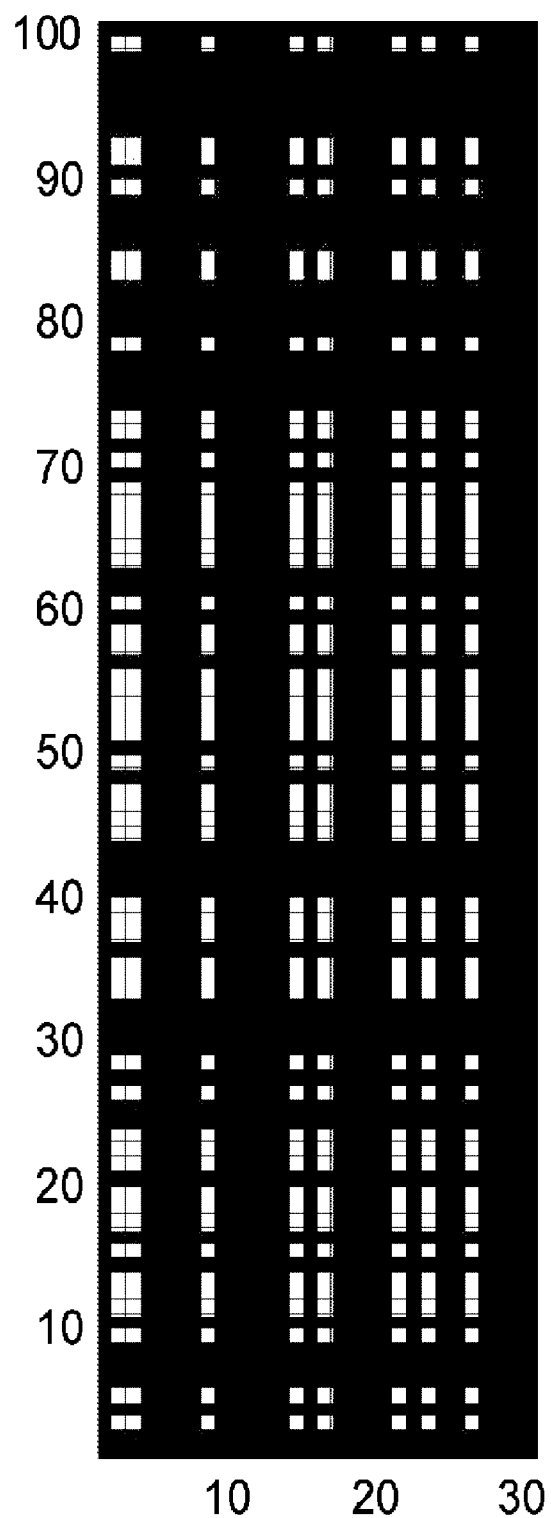
Figure 12C:
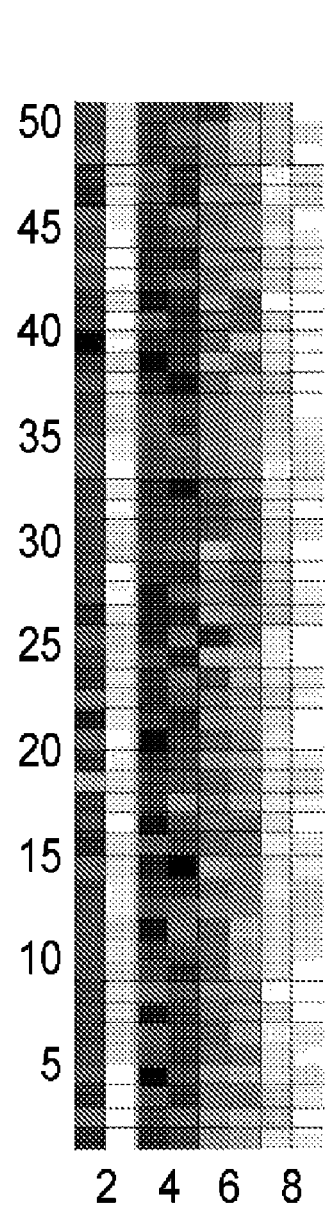
Figure 12D:
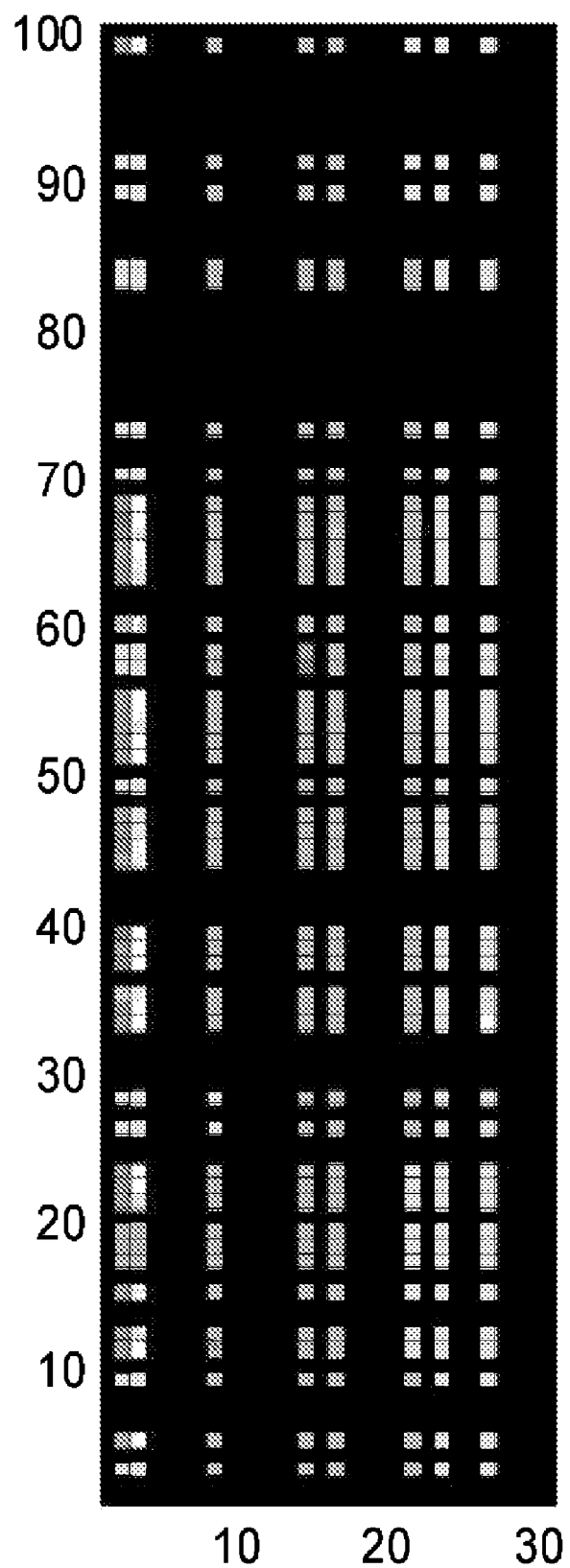
Figure 13A:
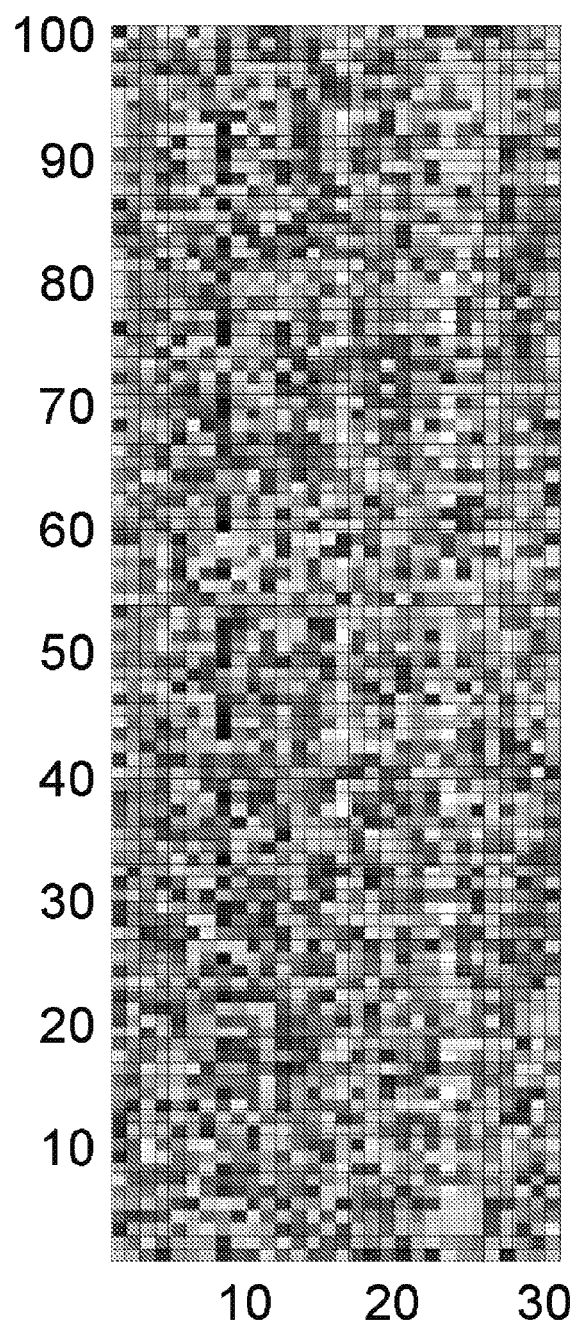
Figure 13B:
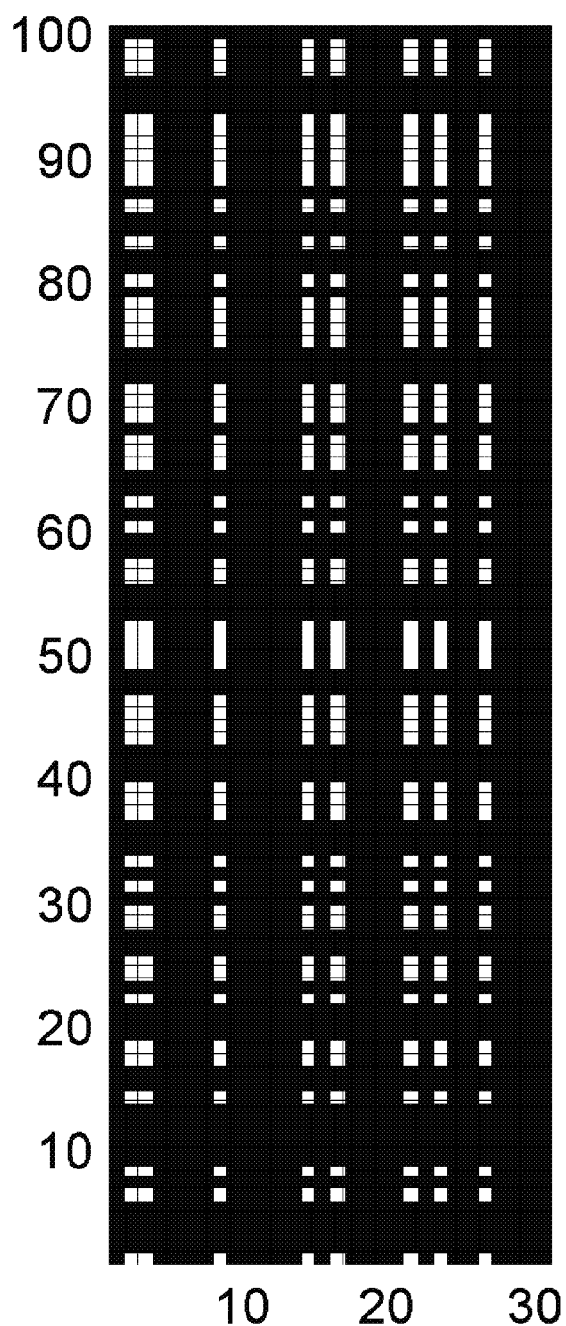
Figure 13C:
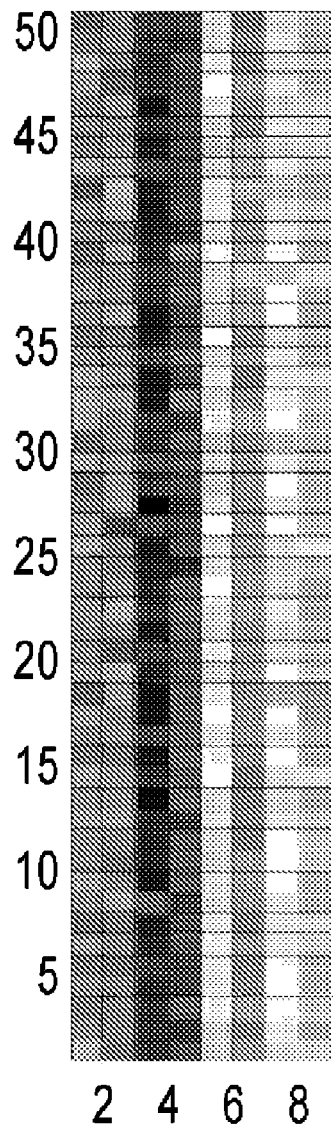
Figure 13D:
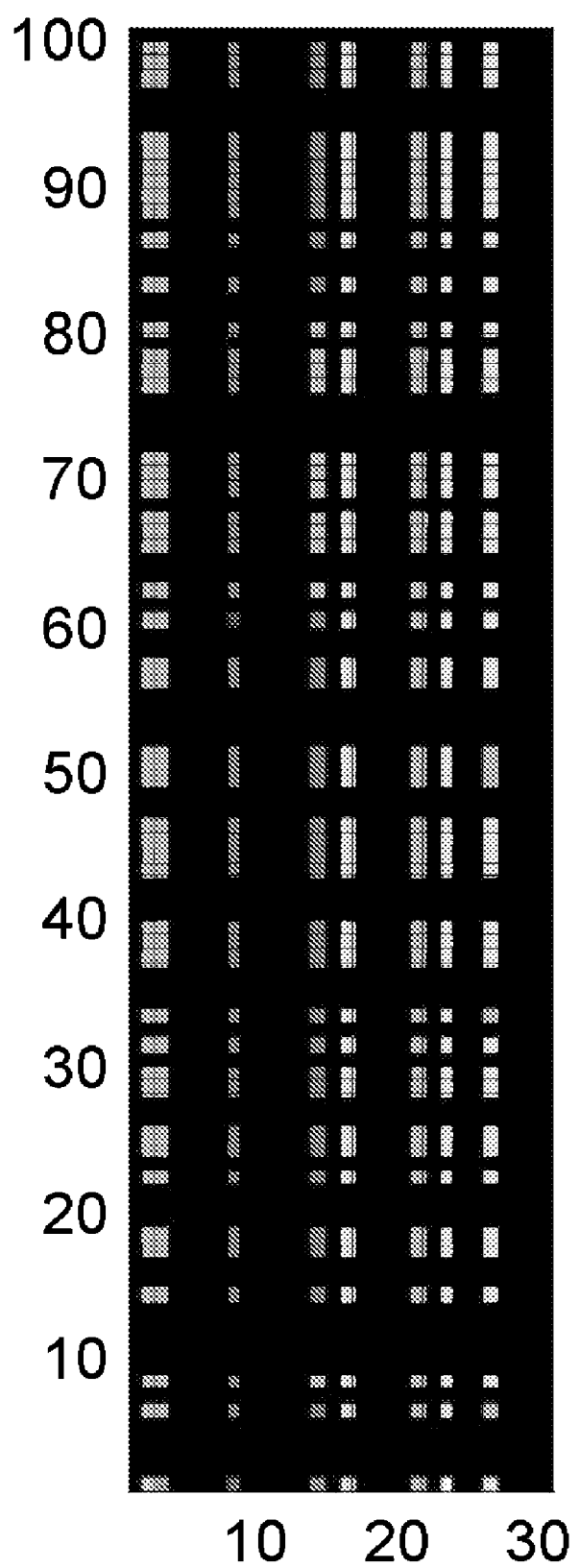
Figure 14A:
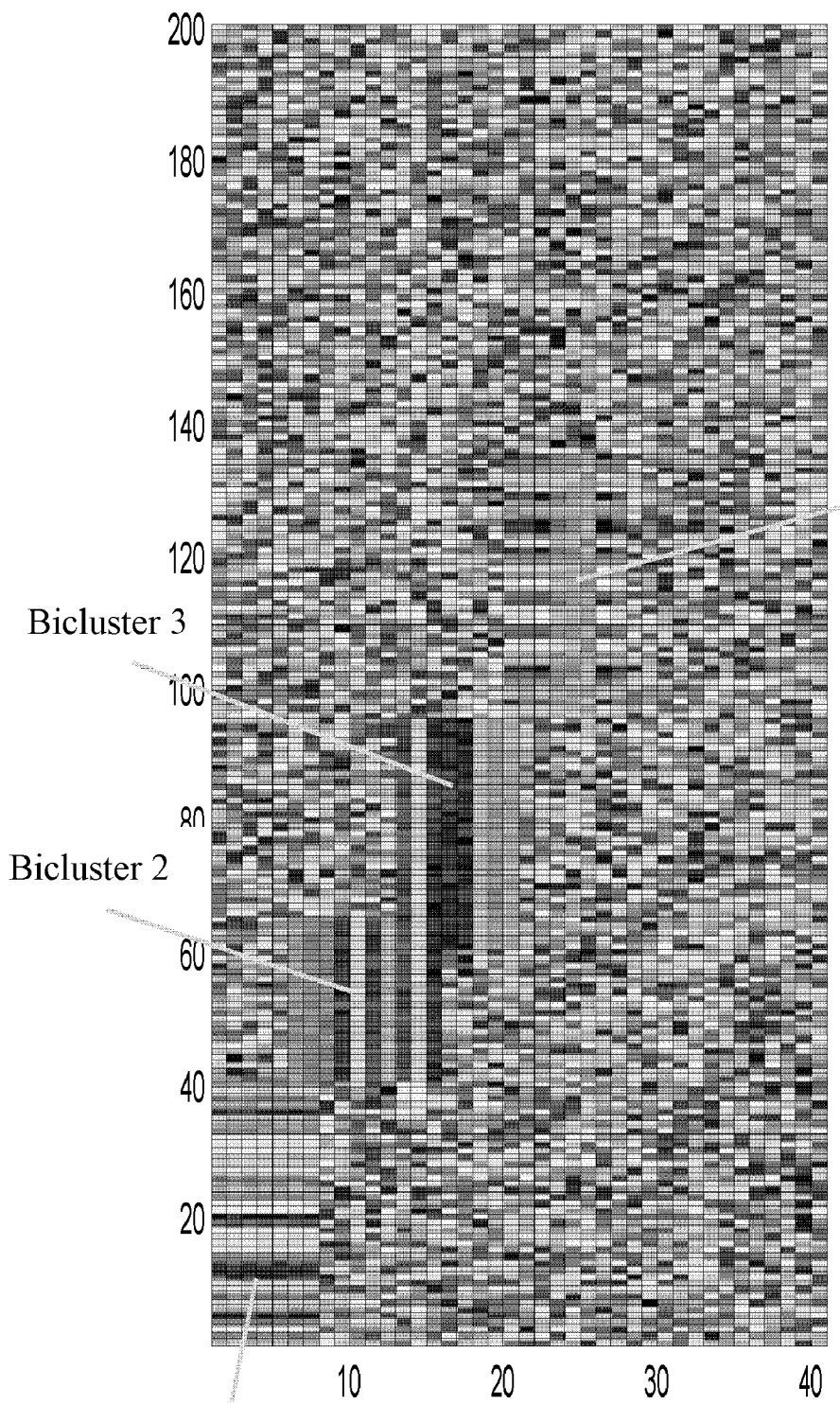
Figure 14B:
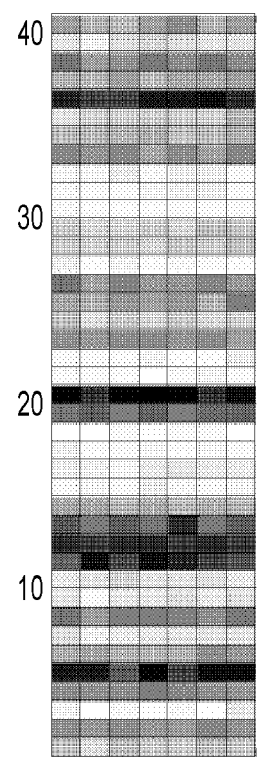
Figure 14C:
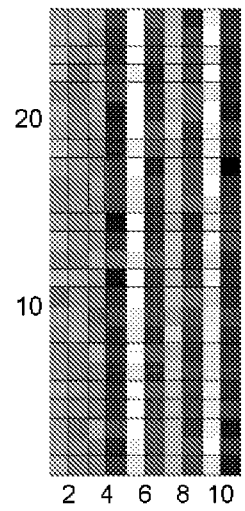
Figure 14D:
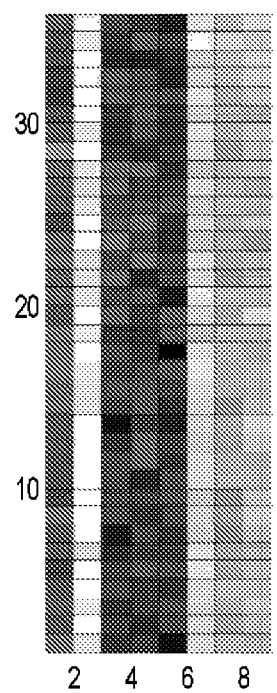
Figure 14E:
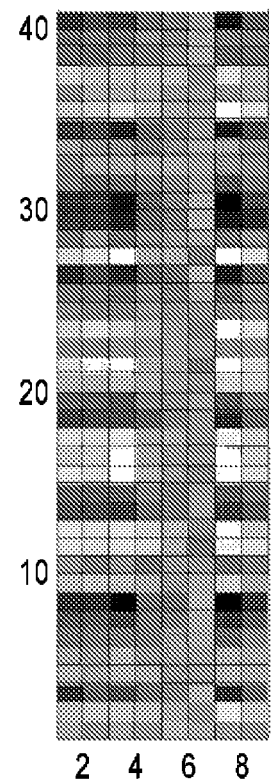
Figure 14G:
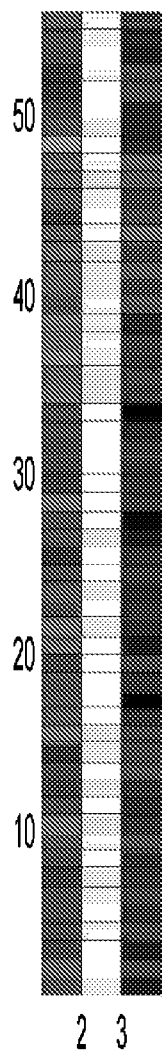
Figure 15:
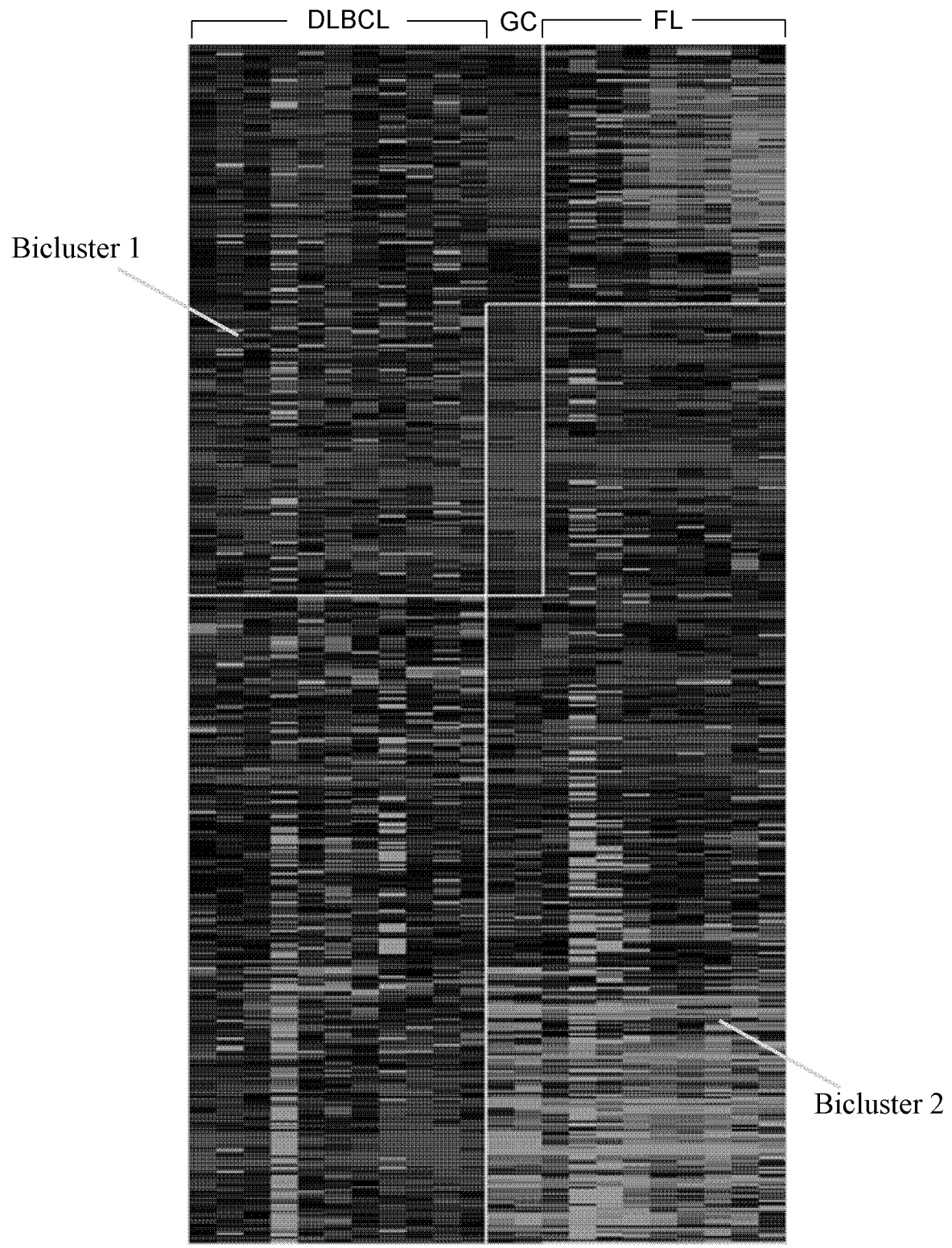
Figure 16:
Figure 17:
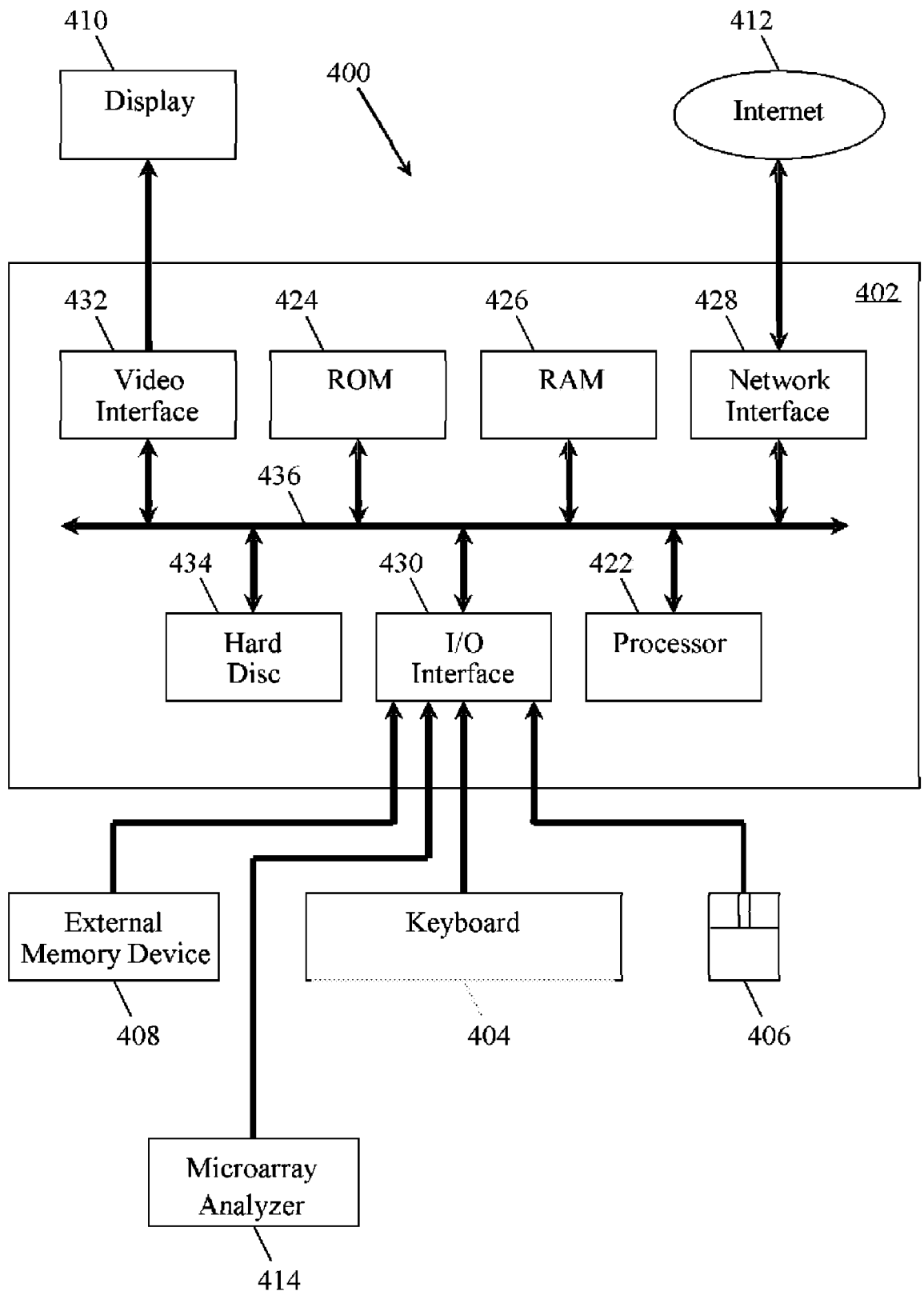

FIGS. 3(a) to 3(f) are portions of data matrices exemplifying several different types of known biclusters;

FIG. 4 is a 3D visualization of a bicluster that covers x and z samples and lies on a plane in (x, y, z) space;

FIGS. 5(a) to 5(f) are representations of some geometries in 3D data space corresponding to certain bicluster patterns;

FIG. 6 is a flowchart relating to an underlying method of an embodiment of the invention;

FIG. 7 is a flowchart relating to a plane detection method of the invention;

FIG. 8 is a flowchart relating to an alternative plane detection method to that of FIG. 7;

FIG. 9 is a flowchart of a geometric bicluster extracting method according to an aspect of the invention;

FIG. 10 is a flowchart for a divide and stitch mechanism allowing larger data sets to use bicluster extracting methods;

FIG. 11 is a graph showing performance test results for an embodiment of the invention when the bicluster is corrupted by noise;

FIGS. 12(a) to 12(d) are synthetic dataset visual matrices used in a first performance analysis;

FIGS. 13(a) to 13(d) are synthetic dataset visual matrices used in a second performance analysis;

FIGS. 14(a) to 14(e) are synthetic dataset visual matrices used in a third performance analysis;

FIG. 14(f) is a graph of multiplicative coefficients of the bicluster of FIG. 14(e);

FIG. 14(g) is a visual matrix of an additional bicluster extracted from the data set of FIG. 14(a);

FIG. 15 are the biclustering results for an embodiment of the invention on the human lymphoma data set;

FIG. 16 are the biclustering results for an embodiment of the invention on the human breast cancer data set; and FIG. 17 is a schematic representation of a computer system according to an embodiment of the invention.

DESCRIPTION

The present invention provides a new approach to dealing with data for analysis as well as, inter alia, a method, apparatus and computer software, etc. for analyzing data, to determine, represent and/or extract biclusters from within such data.

The embodiments below are exemplified using gene expression data, for which the present invention is well suited. However, it is also well-suited for representing and/or extracting biclusters from other data expressed in a matrix or data array, whether two dimensional or higher, such as in collaborative filtering, document indexing, information retrieval from large databases, and analysis of electoral data, consumer spending, foreign exchange rates, and stock market data, where there is a need to classify the data in terms of subsets of features or attributes. A higher dimensional data array can be converted to a 2D array before biclustering. For example, a 3D data matrix with rows as genes, columns as experiment conditions and depths as sub-conditions of each experiment condition can be flattened to become a 2D matrix with columns given by concatenation of depths.

Geometric Interpretation of Biclusters

Although the six patterns in FIGS. 3(a) to 3(f) would appear to be substantially different from each other, treating each sample (column) as a variable in the 4-dimensional (4D) space [x, y, z, w] and each row (gene) as a point in the 4D space, the six patterns in FIGS. 3(a) to 3(f) correspond to the following six geometric structures, respectively:

FIG. 3(a) to a cluster at a single point with coordinate [x, y, z, w]=[1.2, 1.2, 1.2, 1.2];

FIG. 3(b) to a cluster defined by the line x=y=z=w;

FIG. 3(c) to a cluster at a single point with coordinate [x, y, z, w]=[1.2, 2.0, 1.5, 3.0];

FIG. 3(d) to a cluster defined by the line x=y−1=z+1=w−2;

FIG. 3(e) to a cluster defined by the line x=0.5y=2z=(2/3) w; and

FIG. 3(f) to a cluster defined by the line x=0.5(y−0.1)=2 (z−0.1)=(2/3)(w−0.2).

Each gene in a bicluster is a point lying on one of these points or lines when only considering the samples selected by this bicluster.

When the bicluster is embedded in a larger data matrix, the points or lines defined by the bicluster sweep out a hyperplane in a high dimensional data space. This can be visualized geometrically as follows. Assume a three-sample experiment with the samples denoted as x, y, z. If a bicluster covers samples x and z, then there exists a plane on which all data points in the bicluster would lie. The plane is defined by:

$$\beta_1 + \beta_2 x + \beta_4 z = 0 \qquad (1)$$

where $\beta_i$, (i=1, 2, 4) are constant and there is no term $\beta_3$ y since $\beta_3$=0 (the bicluster covers samples x and z for any y). FIG. 4 is a visualization of a bicluster that covers x and z samples and lies on such a plane in the (x, y, z) space.

For gene expression data, the coordinates that would appear in Eq. (1) denote the experimental samples the bicluster covers, and the points on the plane denote the genes in the bicluster.

In general, the different patterns of biclusters discussed above can be uniquely defined by specific geometry (lines or planes) in high dimensional data space. Using the above example of a three-sample experiment with the samples denoted as x, y, z and a bicluster covering samples x and z, three-dimensional (3D) geometric views can be generated for the different patterns, as given in FIGS. 5(a) to 5(f). When the dimension of the data space is higher than three, visualizing the geometric views becomes complicated or even impossible, but the geometric structures are still similar.

FIG. 5 shows six different geometries (lines or planes) in the 3D data space for corresponding bicluster patterns. In each table the shaded columns are covered by the bicluster.

FIG. 5(*a*) shows a bicluster with constant values: represented by one of the lines that are parallel to the y-axis and lie in the plane x=z (the T-plane);

FIG. 5(*b*) shows a bicluster with constant rows: represented by the T-plane;

FIG. 5(*c*) shows a bicluster with constant columns: represented by one of the lines parallel to the y-axis;

FIG. 5(*d*) shows a bicluster with coherent values with additive model: represented by one of the planes parallel to the T-plane;

FIG. 5(*e*) shows a bicluster with coherent values with multiplicative model: represented by one of the planes that include the y-axis; and FIG. 5(*f*) shows a bicluster with coherent values on columns with linear model: represented by one of the planes that are parallel to the y-axis.

Biclustering Using a High Dimensional Geometric Method

The gene expression data is transformed into geometric data in observed data space (feature space) by plotting the data for each row (gene), where each column (sample) represents an axis.

FIG. 6 is a flowchart relating to an underlying method of some aspects of the present invention. These use a geometric gene expression biclustering framework involving two steps:
  (i) detect hyperplanes that exist in the standardized gene expression data as geometric data (step 102); and
  (ii) analyze the hyperplanes for biclusters. This is by analyzing whether a required pattern (that is a pattern that is recognized as a bicluster) exists for the genes which lie in these hyperplanes (step 104).

Plane Detection—Step 102

The Hough Transform (HT) is a powerful technique for line detection in noisy 2-D images and for plane detection in noisy 3-D signals and is widely used in pattern recognition. The HT is a mapping from observed data space into a parameter space. Each feature point in the data space generates "votes" for a set of parameter space points. An area in the parameter space containing many mapped points is suggestive of a hyperplane in the observed data space.

The HT is noise insensitive for line detection in poor quality images. The present invention is able to make use of the realization that the robustness of the HT against noise is especially useful in microarray data analysis since microarray data are often heavily corrupted by noise.

In a microarray experiment, the relative expression levels of N genes of a model organism are probed simultaneously by a single microarray. A series of M arrays probes the expression levels in M different samples (whether under M different experimental conditions or at M time points in the case of measuring temporal changes in expression, etc.).

$\{F_1, F_1, \ldots, F_M\}$ denotes the coordinates of M arrays (samples). For each gene j $\{j=1, 2, \ldots, N\}$, the expression vector is given as $[F_1(j), F_2(j), \ldots, F_M(j)]$.

In 2-D space, a line can be described by $$y = mx + c \qquad (2)$$

where (m, c) are the slope and the intercept of the line with y axis, respectively. However, a problem with the (m, c) parameterization of lines is its inability to describe vertical lines, i.e., $m \to \infty$. Therefore Eq. (2) is only used for lines with $|m| \leq 1$. A second equation which swaps the roles of the x and y axes, $$x = m'y + c' \qquad (3)$$

is used for lines with $|m| > 1$.

With $|m| \leq 1$ and $|m'| < 1$, Eq. (2) and (3) describe all lines in 2-D space without overlap. A similar method can be used to describe hyperplanes in higher dimensional space. In the following description, this parameterization method is used for the hyperplane detection algorithm.

Suppose that among all the observed data $[F_1(j), F_2(j), \ldots, F_M(j)]$, $\{j=1, 2, \ldots, N\}$, there exists a target hyperplane with equation as $$F_M = \sum_{i=1}^{M-1} \beta_i F_i + \beta_M, \qquad (4)$$

where $\{F_1, F_2, \ldots, F_M\}$ are coordinates of points in observed data space and $\{\beta_1, \beta_2, \ldots, \beta_M\}$ are M parameters. A set $\Omega$ is defined with all the indices of the genes which lies on this hyperplane.

For each $j \in \Omega$, $$F_M(j) = \sum_{i=1}^{M-1} \beta_i F_i(j) + \beta_M.$$

The inversion of Eq. (4) indicates that all these points on the target surface satisfy $$\sum_{i=1}^{M-1} F_i(j)\beta_i + \beta_M - F_M(j) = 0 \qquad (5)$$

for all $j \in \Omega$.

The parameters $\{\beta_1, \beta_2, \ldots, \beta_M\}$ are given by the intersection of many hyperplanes given by Eq. (5).

The initial ranges of values $\{\beta_1, \beta_2, \ldots, \beta_M\}$ are taken to be centered at $\{P_1, P_2, \ldots, P_M\}$ and with half-length $\{L_1, L_2, \ldots, L_M\}$, i.e., $\beta_i \in [P_i - L_i, P_i + L_i]$. These ranges $\{\beta_1, \beta_2, \ldots, \beta_M\}$ can be divided into very small "array accumulators" so that each array accumulator can determine a unique array of value $\{\beta_1, \beta_2, \ldots, \beta_M\}$ within acceptable error.

According to the parameterization method in Equation (2) and (3) above, $|\beta_i| \leq 1$, $\{i=1, \ldots, M-1\}$. That means $P_1 = P_2 = \ldots = P_{M-1} = 0$, $L_1 = L_2 = \ldots = L_{M-1} = 1$. By defining $\psi = \min(F_M) - \max(|F_1|) - \Lambda - \max(|F_{M-1}|)$ and $\xi = \max(F_M) + \max(|F_1|) + \Lambda + \max(|F_{M-1}|)$, it is easy to get $\psi \leq \beta_M \leq \xi$. This then gives $$P_M = \frac{\xi + \psi}{2} \text{ and } L_M = \frac{\xi - \psi}{2}.$$

In above case, the whole observed data space is searched for the hyperplane. So the computational cost is heavy. However, if there is some a priori knowledge about the target hyperplanes or the search is only interested in part of hyperplanes in the data, one can use a more narrow interval for $\{\beta_1, \beta_2, \ldots, \beta_M\}$, such as $0 \leq \beta_1 = \beta_2 = \ldots = \beta_{M-1} \leq 1$. This can reduce the computational cost.

According to Eq. (5), one feature point in the observed data space is mapped into many points (e.g., a hyperplane) in parameter space. An accumulator in the parameter space containing many mapped points (e.g., the intersection of many hyperplanes) reveals a potential feature of interest.

A suitable HT-based plane detection method includes three steps, as shown in FIG. 7:
(i) formulating a parameter space hyperplane as Eq. (5) (step 110);
(ii) dividing the parameter space into accumulators which are small enough so that the desired resolution is satisfied (step 112); and
(iii) for each accumulator, let every point in the observed data make a vote (step 114). If the votes that an accumulator receives are more than a selected threshold, a hyperplane is detected in the observed data space as Eq. (4) and the value of $\{\beta_1, \beta_2, \ldots, \beta_M\}$ are given by the accumulator.

Hyperplane Formulation—Step 110

The HT does not use Eq. (5) directly.

Taking the initial ranges of value $\{\beta_1, \beta_2, \ldots, \beta_M\}$ to be centered at $\{P_1, P_2, \ldots, P_M\}$ with half-length $\{L_1, L_2, \ldots, L_M\}$, allows Eq. (5) to be rewritten as:

$$\sum_{i=1}^{M-1} \frac{F_i(j)L_i}{W(j)L_M} \frac{\beta_i}{L_i} + \frac{\beta_M}{W(j)L_M} - \frac{F_M(j)}{W(j)L_M} = 0 \quad (6)$$

for all $j \in \Omega$, where $W(j)$ is a weighting scale used to ensure that $\Sigma_{i=1}^{M} a_i^2(j) = 1$ [see below for definition of $a_i(j)$] (normalization).

Let $$X_i = \frac{\beta_i}{L_i} \quad (i = 1, \ldots, M)\text{(hyperplane variables)},$$

$$\frac{F_i(j)L_i}{W(j)L_M} = a_i(j) \quad (i = 1, \ldots, M-1)\text{(hyperplane coefficients)},$$

$$a_M(j) = \frac{1}{W(j)}.$$

and $$a_{M+1}(j) = -\frac{F_M(j)}{W(j)L_M}$$

Eq. (6) can then be rewritten as $$\sum_{i=1}^{M} a_i(j)X_i + a_{M+1}(j) = 0 \quad (7)$$

for all $j \in \Omega$.

In fact, it is not necessary for the dimension of the parameter space X to be equal to the dimension of observed signal, M. k can be used to replace M for a more general expression $$\sum_{i=1}^{k} a_i(j)X_i + a_{k+1}(j) = 0 \quad (8)$$

for all $j \in \Omega$ where $X_i$ is the i-th dimension of the parameter space. Each $a_i(j)$ is a function of observed feature points and is normalized such that $\Sigma_{i=1}^{k} a_i^2(j) = 1$. The initial range of each $X_i$ is the interval given by $[P_i/L_i - 1, P_i/L_i + 1]$ centered at $P_i/L_i$. All these ranges will comprise a hypercube in the parameter space $(X_1, \ldots, X_k)$.

Dividing Parameter Space into Accumulators—Step 112

Once the parameter space has been formulated, it is divided evenly up into equal size blocks or hypercubes in each direction, with each hypercube having an associated accumulator. The number of hypercubes depends on the required resolution, as discussed below.

Vote Counting Scheme—Step 114

For each accumulator, every point in the observed signals needs to vote. Each accumulator corresponds to a set of range values $(X_1, X_2, \ldots, X_k)$. For each point j in the observed data, if $$\sum_{i=1}^{k} a_i(j)X_i + a_{k+1}(j) = 0$$

can be satisfied when the values $(X_1, X_2, \ldots, X_k)$ lie in this accumulator, it will give a vote to this accumulator. An accumulator receiving votes more than a threshold reveals a corresponding hyperplane in the observed data space.

So, to determine whether an accumulator receives a vote from a point j in observed signals, it is only necessary to determine whether a hypercube (accumulator) intersects with a particular hyperplane $$\sum_{i=1}^{k} a_i(j)X_i + a_{k+1}(j) = 0.$$

To speed up this test from the standard HT, a simpler conservative test can be used to check whether the hyperplane intersects the hypercube's circumscribing hypersphere. Assume the center of the accumulator is at $[C_1, \ldots, C_k]$. r is the radius of the hypersphere, the testing criterion is whether $$a_{k+1}(j) + \sum_{i=1}^{k} a_i(j)C_i \leq r \quad (9)$$

If Eq. (9) is satisfied, gene j gives a vote to the corresponding accumulator.

If a vote count threshold is set, those accumulators having a vote count higher than the threshold are investigated further to determine if they represent hyperplanes in the observed data space. This is described later.

However, whilst the standard HT can be used in the present invention to detect planes, it requires large computational complexity and storage requirements for more than 3 dimensions, making it less useful in many circumstances. As such, the Fast Hough Transform (FHT) (described in Li, H., Lavin, M. A., and Master, R. J. L. (1986) Fast Hough Transform: a hierarchical approach. Computer Vision, Graphics, and Image Processing, 36, 139-161) may be preferred. This algorithm is used on the gene expression data as a plane detection algorithm. It gives considerable speedup and requires less storage than the conventional HT. The FHT has very simple and efficient high-dimensional extension. Furthermore, the FHT uses a coarse-to-fine mechanism which provides good noise resistibility.

The three-step HT-based plane detection method of FIG. 7, can be replaced with a two-step FHT-based plane detection method of FIG. 8, in which the last two steps are replaced with a single recursive step in which voting and allocating accumulators are restricted to relevant, increasingly smaller hypercubes.
  (i) formulating a parameter space hyperplane as Eq. (5) (step 110—as before);
  (ii) recursively divide the parameter space and allocate accumulators and count votes for relevant hypercubes (step 116)

Allocating Accumulators and Vote Counting—Step 116)
  K-Tree Representation

The HT-based plane detection method of FIG. 7 divides the parameter space up directly into very small accumulators. On the other hand, the FHT algorithm recursively divides the parameter space into hypercubes from low to high resolutions. Only where a hypercube has votes exceeding a selected threshold does the FHT perform subdivision, and subsequent further "vote counting". This hierarchical approach leads to a significant reduction in both computational time and storage space compared to the conventional HT.

For the FHT, the parameter space is represented as a nested hierarchy hypercube. A k-tree is associated with the representation. The root node of the tree corresponds to a hypercube covering the whole parameter space of the formulated hyperplane (step 110) centered at vector $C_0$ with side-length $S_0$. Each node of the tree has $2^k$ children arising when that node's hypercube is halved along each of its k dimensions. Each child has a child index, a vector $b=[b_1, \ldots, b_k]$, where each $b_i$ is $-1$ or $1$.

The child index is interpreted as follows: if a node at level l of the tree has center $C_l$, then the center of its child node with index $[b_l, \ldots, b_k]$ is $$C_l + \frac{S_{l+1}}{2} b \qquad (10)$$

where $S_{l+1}$ is the side length of the child at level l+1 and $S_{l+1}=S_l/2$.

Since this embodiment uses a coarse-to-fine mechanism, for each accumulator at different levels a test is made using Eq. (9). For an accumulator of level l, the radius of its circumscribing hypersphere r equals to $\sqrt{k}S_l/2$.

Based on the K-tree structure, an incremental formula can be used to calculate the left part of Eq. (9). Dividing the left part of Eq. (9) with $S_l$, the normalized distance can be computed incrementally for a child node at each level with child index $[b_1, \ldots, b_k]$ as follows:

At top level $$R_0(j) = \frac{a_{k+1}(j)}{S_0} + \sum_{i=1}^{k} a_i(j) \cdot \frac{C_0(i)}{S_0} \qquad (11)$$

At level l $$R_l(j) = 2R_{l-1}(j) + \frac{1}{2}\sum_{i=1}^{k} a_i(j) b_i \qquad (12)$$

Test (9) can now be expressed as:
  for the gene j and a child node with child index $[b_1, \ldots, b_k]$ at level l, if $$|R_l(j)| \leq \sqrt{k}/2, \qquad (13)$$

(i.e. the hyperplane intersects the cube) gene j will generate a vote for this child node.

According to the above analysis, the FHT is a mapping from an observed data space into a parameter space. Each feature point in the data space generates "votes" for a set of sub-areas (hypercubes) in the parameter space. A sub-area in the parameter space that received many votes reveals the feature of interest. The FHT algorithm recursively divides the parameter space into hypercubes from low to high resolutions. It performs the subdivision and the subsequent "vote counting" is done only in hypercubes with votes exceeding a selected threshold. A hypercube with acceptable resolution and with votes exceeding a selected threshold indicate a detected hyperplane in the observed data.

Geometric Biclustering

FIG. 9 is a flowchart of a geometric bicluster extracting method according to an aspect of the invention, when given a set of genes expression data $[F_1(j), F_2(j), \ldots, F_M(j)]$, j=1, 2, ..., N under diverse experimental conditions.

Step 202—Determine Parameters, Including:
  (a) A minimum vote count "T" as threshold and a desired finest resolution "q".

The minimum vote count "T" denotes the minimum number of genes in a bicluster. It depends on the experiment objective and may be selected by the user. For example, the minimum may be 4.

The desired finest resolution "q" depends on the significance of the noise in the data. For a perfect bicluster (a perfect constant bicluster means that all values are equal), "q" can be arbitrarily big, that is, one can use an arbitrarily finest resolution. However, in a real case, the perfect bicluster is often useless and "q" reflects how significant noise is permitted in the bicluster detected. If it is hoped that the biclusters that will be detected are closer to the perfect bicluster, q should be a bigger number.

In many case, one has no knowledge about the noise in the data. It is acceptable to use a try-and-use method to select q. The FHT uses a coarse-to-fine mechanism. In a coarse resolution, there are few accumulator cells and the number of hyperplanes detected is small. At a finer resolution, there are more accumulator cells. However, in the finer resolution, the accumulator cells are smaller and it is more difficult for a feature point to generate a hit; thus many accumulators cannot gain enough votes (exceeding the threshold) to ensure the existence of the corresponding hyperplane. So, if a too large value is select for q, fewer hyperplanes will be detected. Hence, q can be tested starting from a small value and increasing gradually until there are plenty of hyperplanes detected.

(b) A transformation that maps gene expression data $[F_1(j), F_2(j), \ldots, F_M(j)]$ into a hyperplane in the parameter space represented by $$\sum_{i=1}^{k} a_i(j)X_i + a_{k+1}(j) = 0$$

for $j = 1, 2, \Lambda, N$.

(c) The initial bound of each $X_i$ and the root hypercube, based on the transformation.

The initial bound of each $X_i$ can readily be determined since it is already known that $\{\beta_1, \beta_2, \ldots, \beta_M\}$ are taken to be centered at $\{P_1, P_2, \ldots, P_M\}$ and with half-length $\{L_1, L_2, \ldots, L_M\}$. and that $$X_i = \frac{\beta_i}{L_i}$$

(i=1, ..., M) (hyperplane variables).

Assuming $X_i$ lies in an interval $[\alpha_i, \beta_i]$, the root hypercube are $\{[\alpha_1, \beta_1], [\alpha_2, \beta_2], \ldots, [\alpha_M, \beta_M]\}$.

Step 204 Transform gene expression data into the parameter space using the transformation derived in part (b) of step 202.

Step 206 Perform the voting procedure for each node, having first computed the normalized distance from the hyperplane to each node. Initially, the only node is the root node. For each gene, for each node, if Eq. (13) is satisfied, add one to the vote count of the relevant node.

Step 208 Determine if the vote count for any current level node is larger than the threshold T and the resolution is coarser than q.

If the determination at step 208 is positive, then for each relevant node:

Step 210 Subdivide the node into the K-tree child nodes and revert to step 206.

This vote-and-subdivide mechanism is performed for each new node until no new node appears, at which point the determination at step 208 is negative, at which point the method proceeds to:

Step 212 Determine if there is more than 1 node with the finest resolution q and a vote count larger than T.

If the determination at step 212 is negative, then proceed with the node with the best resolution, and with the highest vote count if there is more than one node with the same best resolution:

Step 214 Record that node. This is the most probable solution for the existence of a hyperplane and hence a bicluster in the observed data.

If the determination at step 212 is positive:

Step 216 When there are several nodes with resolution equal to q and vote counts larger than T, collect the hyperplanes in the observed data space associated with these nodes and which have the same genes into bundles. In the FHT, a node (accumulator) denotes a unique hyperplane in the observed data space.

Step 218 For each bundle of hyperplanes in observed data space, check for biclusters by checking the common samples (variables) and compare the hyperplanes with the models corresponding to different types of biclusters. Hyperplanes in a bundle that are not consistent with any patterns in FIGS. 3(*a*) to 3(*f*) or a corresponding bicluster that covers too few samples are discarded. It may vary, but exemplarily the minimum requirements for a bicluster are 4 rows (genes), otherwise there may not be enough points on the hyperplane and 2 columns (samples). This step corresponds to step 104 of FIG. 6.

Step 220 Output, as biclusters, those bundles for which biclusters are found and not discarded.

This specific embodiment uses an approach based on the method described with reference to FIG. 8. However, the invention is not limited thereto. For instance steps 206 to 212 may be replaced with steps 112 and 114 of the method described with reference to FIG. 7, with an intervening step prior to step 216 of outputting all hypercubes with and a vote count larger than T.

A Divide-and-Stitch Extension for Very Large Microarray Data Set

Microarray data sets can now contain thousands of genes and hundreds of samples. Although the biclustering algorithm above can process moderate size data sets, for data sets of very big size, extra effort is necessary.

A divide-and-stitch mechanism, as shown in FIG. 10, can be used to facilitate the processing:

Step 302 pre-cluster the samples;

Step 304 divide the samples into several non-overlapping blocks, each block including data from all genes but for different samples;

Step 306 perform bicluster extraction for each block, for instance as described above with reference to FIG. 9;

Step 308 for a detected bicluster in a block, examine whether samples from other blocks can be incorporated into it;

Step 310 delete any duplicated biclusters; and

Step 312 output biclusters from the whole data set.

In this divide-and-stitch mechanism, if all samples in a possible bicluster are divided to the same block, the performance of this divide-and-stitch method is the same as using extracting the biclusters on the whole data set, globally. However, the act of dividing the data into different blocks can actually destroy some of the biclusters (putting different samples from the same biclusters into different blocks). This is a possibility for those biclusters containing only (2×the number of blocks) samples or fewer. Any more than that number and at least one block will contain the minimum of two samples to be recognized as a bicluster. Step 302 is therefore a useful option to reducing even this possibility. This preprocessing method: clusters the samples in the data set using a hierarchical clustering method before the division step (step 304) (for instance the Eisen et al. method mentioned in the earlier part of this specification). Since only samples are clustered into different blocks, such preprocessing can be very simple and fast.

An alternative to such pre-processing is to conduct bicluster extraction several times, each time the blocks containing different combinations of samples, then compare the results. Alternatively, or additionally, the data can be divided up into overlapping blocks.

To evaluate the effectiveness of the divide-and-stitch mechanism, it was tested using simulated data. A synthetic data set of size 100 by 30 with different types of biclusters embedded was provided. The bicluster extraction method of FIG. 9 was used on the whole data set, using FHT. Then biclustering was performed again, using the method of FIG. 10, dividing the data set into 10-column blocks. In all the experiments, the difference between the two methods was trivial. The worst situation of a bicluster being divided up so much as not to be detected was not observed.

In a real data set, the situation is more complex. It is inevitable that this divide-and-stitch mechanism will degrade the algorithm. To reduce this problem, it is desirable to be able to analyze larger data sets without having to resort to divide and stitch. One solution is to use more powerful and faster algorithms for high-dimensional hyperplane detection or use other variants of the HT, such as probabilistic Hough Transform (Kiryati, N. Eldar, Y. and Bruckstein, A. M. (1991) A Probabilistic Hough Transform, Pattern Recognition, 24, 303-316.) and random Hough Transform (Xu, L. and Oja, E., (1993) Randomized Hough Transform (RHT): Basic Mechanisms, Algorithms, and Computational Complexities, CVGIP: Image Understanding, 57, 131-154.).

The present invention can also use special hardware or parallel computer algorithms. Since HT is a very popular algorithm and has been widely used in astronomy, medical imaging and pattern recognition, there are many implementations available. Further, a parallel algorithm is also discussed in Li, H., Lavin, M. A., and Master, R. J. L. (1986) Fast Hough Transform: a hierarchical approach. Computer Vision, Graphics, and Image Processing, 36, 139-161.

Experimental Results

Results are presented based on performing various the above described method of FIG. 9 on several synthetic and real data sets. In microarray experiments, the gene expression data set is often degraded by noise. So the noise resistibility was examined using simulated data. Since the presented algorithm is able to detect different types of biclusters, biclustering experiments were performed to detect the following patterns in a synthetic data set: constant columns, constant rows and coherent values with multiplicative models. Synthetic data was also used with four overlapped biclusters to examine the ability of the algorithm for finding multiple biclusters, especially when overlaps between biclusters are present. Finally, results are presented from using the algorithm on two real microarray gene expression data sets.

First Performance Analysis

Synthetic Data—Bicluster Corrupted by Noise of Same Variance for All Samples

A bicluster pattern of 50 rows by 8 columns was embedded into a data set of size 100 by 30. The background of the data set, that is the whole data set except where the bicluster was embedded, was generated from the uniform distribution U(−5, 5). The embedded bicluster pattern contained constant columns and the value of each column was random and produced from a uniform distribution U(−5, 5). Gaussian noise with variance from 0.1 to 1 was generated to degrade the bicluster.

In all these experiments, all the columns (samples) where the embedded pattern was actually located were correctly found. The results of the performance test in terms of the number of correctly detected genes in terms of the noise variance is given in FIG. 11. With synthetic data the number of biclusters can be known exactly, thus allowing a base-line comparison to be made when noise is added before performing bicluster extraction according to the present invention.

The results of a specific experiment with the bicluster data corrupted by Gaussian noise with variance equalto 0.8 are shown in FIG. 12. FIG. 12(*a*) is a 100 by 30 synthetic data matrix used in the performance analysis. FIG. 12(*b*) shows the positions of all elements in the bicluster hidden in the data matrix of FIG. 12(*a*). FIG. 12(*c*) is the bicluster pattern itself.

FIG. 12(*d*) shows the pattern and the element positions of the bicluster that were extracted. All the relevant samples were detected while 4 genes were missed in the bicluster detected.

The algorithm missed some of the genes probably due to performance limitations. For a dataset degraded by noise, it is possible that in some points (especially for a point where the magnitude of the original signal is small), the magnitude of noise is significantly large compared to the magnitude of the original signal.

To evaluate the robustness of the algorithm, the algorithm was tested on data sets sampled randomly, rather than on the whole data set.

In a first experiment, 50 gene expression profiles (rows) were randomly sampled from the data set in FIG. 12(*a*) to form a new 50×30 sampled data set. This was carried out 100 times, each time randomly, to obtain 100 sampled data sets in this manner. The method described with reference to FIG. 9 was used on the sampled data sets with threshold T=20. The bicluster was correctly detected in 96 sampled data sets.

In the second experiment, 15 samples were randomly selected from the data set in FIG. 12(*a*) to form a new 100×15 sampled data set. This was carried out 100 times, each time randomly, to obtain 100 sampled data sets in this manner. The method described with reference to FIG. 9 was used on the sampled data sets with threshold T=50. The bicluster was correctly detected in 95 sampled data sets.

These results show that the invention, particularly as exemplified works well for noisy data.

Second Performance Analysis

Synthetic Data—Bicluster Corrupted by Noise of Different Variance Among Samples

For the above experiment, the noise in the bicluster had the same variance for all samples. In practical applications, there may be different variances for different samples. Fortunately, the exemplified algorithm can deal with this easily. In the derivation of the algorithm described above, there is a normalization, $a_i(j)$, related to the values of $\{L_1, L_2, \ldots, L_M\}$. By selecting different parameters for these variables, the noise in $a_i(j)$ can be rescaled to a same variance. For example, if the variance of the noise in $\{F_1, F_3, \ldots, F_M\}$ are 1 while the variance of the noise in $F_2$ is 2. Then, using $\sqrt{2}L_2=L_1=L_3 \ldots = L_{M-1}$ actually detects the biclusters in $\{F_1, F_2/2, \ldots, F_M\}$, where the noise variance is now equal for all samples.

A bicluster pattern of 50 rows by 8 columns was embedded into a data set of size 100 by 30. The background was again generated from the uniform distribution U(−5, 5). The pattern contained constant columns and the value of each column was random and produced from a uniform distribution U(−5, 5). Gaussian noise with variance 0.6 was generated to degrade the first seven samples in the bicluster and Gaussian noise with variance 0.9 was generated to degrade the remaining samples. The experiment was performed on the data set as a whole with T=50. The results of the experiment are shown is FIGS. 13(*a*) to 13(*d*).

FIG. 13(*a*) is a 100 by 30 data matrix. FIG. 13(*b*) shows the positions of all elements in the bicluster hidden in the data matrix of FIG. 13(*a*). FIG. 13(*c*) is the bicluster pattern itself. FIG. 13(*d*) shows the pattern and the element positions of the bicluster that were extracted. All the relevant samples were detected while 2 genes were missed.

First Performance Analysis

Synthetic Data with Multiple Overlapping Biclusters

To show that the algorithm can successfully detect biclusters of different types and to examine the ability of the algorithm to find multiple biclusters simultaneously, especially when overlap between biclusters is present, four biclusters were embedded into a noisy background generated by a uniform distribution U(−5, 5). Gaussian noise with variance equal to 0.3 was generated to degrade the bicluster data. FIG. 14(a) is the resulting 200 by 40 data matrix, using T=25.

The four embedded biclusters had the following sizes: 40 by 7 for Bicluster 1 (FIG. 14(b)) of constant row, 25 by 10 for Bicluster 2 (FIG. 14(c)) of constant column, 35 by 8 for Bicluster 3 (FIG. 14(d)) of constant column, 40 by 8 for Bicluster 4 (FIG. 14(e)) of multiplicative coherent values with the multiplicative coefficients for each row given in FIG. 14(f). As can be seen in the main plot of FIG. 14(a), Bicluster 1 overlapped with Bicluster 2 in two columns, and Bicluster 3 overlaps with Bicluster 2 in five rows and three columns. Randomizing row and column permutations are then performed on FIG. 14(a) to obtain a final test data set (not shown). The locations of the biclusters were noted during the randomization process and they serve as ground truth allowing the results to be validated.

In this experiment, bicluster 1 was found with all 7 samples and 40 rows. Bicluster 2 is found with 10 samples and 25 rows. Bicluster 3 is found with 8 samples and 35 rows. Bicluster 4 is found with 8 samples and 40 rows. All four biclusters were perfectly detected. An unexpected outcome was that a new bicluster with 3 samples and 60 rows was also detected (FIG. 6(g)). This bicluster was located at the overlap position of Bicluster 2 and Bicluster 3 and comprised the last three columns of Bicluster 2 and first three columns of Bicluster 3 and all rows of the two biclusters. This new bicluster was a valid bicluster by itself, even though it was completely overlapped by Biclusters 2 and 3. The detection of this (somewhat unexpected) new bicluster further shows the efficacy of this algorithm in handling overlapping biclusters.

Human Lymphoma Data Set

In this experiment, the algorithm was applied to the lymphoma data set (Alizadeh, A. A. et al. (2000) Distinct types of diffuse large B-cell lymphoma identified by gene expression profiling. Nature, 403, 503-511). This data set is characterized by well defined expression patterns differentiating three types of lymphoma: diffuse large B-cell lymphoma (DLBCL), chronic lymphocytic leukaemia (CLL) and follicular lymphoma (FL). The data set consists of expression data from 128 lymphochip microarrays for 4026 genes in 96 normal and malignant lymphocyte samples. The missing values in the data set are imputed using a project-onto-convex-sets algorithm (Gan, X., Liew, A. W. C., and Yan, H. (2006) Microarray Missing Data Imputation based on a Set Theoretic Framework and Biological Knowledge. *Nucleic Acids Res.*, 34(5): 1608-1619). No other preprocessing was necessary.

The results of the experiment are shown in FIG. 15, which are the biclustering results for the human lymphoma data set.

For this data set, existing hierarchical clustering, for example by the Eisen et al. method, results in germinal center tissues buried within the DLBCL class (Alizadeh et al. 2000). However, using the present biclustering algorithm, the germinal center (GC) tissues are biclustered with both the DLBCL and FL tissues, as shown in FIG. 15, thereby uniquely characterizing them as a distinct class. In the bicluster associated with DLBCL tissue (cluster 1), there are 298 genes. In the bicluster associated with FL tissue (cluster 2), there are 349 genes. There are 156 genes in the overlapping region of these two biclusters. Tanay, A., Sharan, R. and Shamir, R. (2002) Discovering statistically significant biclusters in gene expression data. Bioinformatics, 18 (Suppl. 1), 136-144, pointed out that this type of biclustering can help characterize the data uniquely as a distinct class. Compared to Tanay et al.'s algorithm, more genes are detected in the present biclustering result.

The genes in these two biclusters can be annotated using the Duke Integrated Genomics Database (Delong, M. et al., (2005) DIG—a system for gene annotation and functional discovery. *Bioinformatics*, 21(13), 2957-2959.). Gene Ontology (GO) terms (The Gene Ontology Consortium. (2000) Gene ontology tool for the unification of biology. *Nat. Genet.*, 25, 25-29) for cellular components may be identified and the distribution of genes is obtained by counting the number of genes in each bicluster for each GO category. The 10 main relevant categories are: cell, cellular component unknown, envelope, extracellular matrix, extracellular region, membrane-enclosed lumen, organelle, protein complex, synapse, and virion. In bicluster 1, 48.32% of the genes are not GO annotated, 49.11% of the genes have GO related to cell, 33.22% of the genes have GO related to organelle. In bicluster 2, 53.86% of the genes are not GO annotated, 41.39% of genes have GO related to cell, 19.21% of the genes have GO related to organelle. Note that some genes can belong to more than one cellular component. Hence, the percentage numbers in a bicluster can sum up to more than 100%. Moreover, 3.96% of the genes in bicluster 1 have GO related to extracellular matrix while none of the genes in bicluster 2 are related to this component; and 4.36% of the genes in bicluster 2 have GO related to extracellular region while none of the genes in bicluster 1 are related to this component. In addition, the 27 genes with GO related to protein complex exist only in bicluster 1 and in the intersection of the two biclusters.

Human Breast Cancer Data

In this experiment, the algorithm was applied to the breast cancer data set (van 't Veer, L. J. et al. (2002) Gene expression profiling predicts clinical outcome of breast cancer. *Nature*, 415, 530-536. ). This is a rather complicated data set. The original data set includes ~20000 genes and 98 breast tumors. Van 't Veer et al, 2002, identified ~5000 genes as significantly regulated across the group of samples and were used for subsequent clustering analysis. Using existing hierarchical methods, 98 breast tumors can be classified into two clusters: in the first cluster, 34% of the sporadic patients were from the group who developed distant metastases within 5 years; in the second cluster, 70% of the sporadic patients had a progressive disease.

FIG. 16 is a biclustering result of the present approach for the human breast cancer data set. The biclustering algorithm was applied to ~5000 genes. The divide-and-stitch mechanism is used for biclustering this data set. Two biclusters of constant values are shown in FIG. 16. In bicluster 1, there are 1013 genes and 34 tumors (29 belong to the poor prognosis group: 17 from patients with BRCA1 germ line mutations and 12 from patients who developed distant metastaset within 5 years.). In the bicluster 2, there are 642 genes and 42 tumors (32 belong to the poor prognosis group: from patients who continued to be disease-free after a period of at least 5 years). These two biclusters includes 214 genes which have been used as "prognosis classifier" in (van 't Veer et al, 2002), covering 92.6% genes of all.

The genes in these two biclusters are then also annotated by using the Duke Integrated Genomics Database. The 11 main relevant GO categories are: biological process unknown, cellular process, development, growth, interaction between organisms, physiological process, pigmentation, regulation of biological process, reproduction, response to stimulus, and viral life cycle. In bicluster 1, 41.66% of the genes are not GO annotated, 51.14% of the genes have GO related to cellular process, 49.26% of the genes have GO related to physiological process, 13.03% of the genes have GO related to regulation of biological process. In bicluster 2, 56.54% of the genes are not GO annotated, 37.69% of the genes have GO related to cellular process, 35.05% of the genes have GO related to physiological process, 11.06% of the genes have GO related to regulation of biological process. In addition, a major difference between the two biclusters is that 12.24% of the genes (124 genes) in bicluster 1 have GO related to response to stimulus while only 0.93% (6 genes) of the gene in bicluster 2 are related to this process. From these results, it can be seen that biclustering can produce biologically relevant grouping of genes.

Although the above discussion is exemplified byway of gene expression data, the invention is not limited thereto, as has been mentioned before. For example, an array of reaction products which vary according to pressure and temperature levels might show subsets of temperatures that behave in a pattern for certain pressures. Another example would be an array of the level of various, apparently free-floating, currencies against the US dollar, measured over a period of time (for instance on the first day every month for 10 years) might lead to a subset of those currencies that have consistent up-and-down changes in a subset of months.

Embodiments of the invention may be implemented, inter alia, using just hardware, with circuits dedicated for the required processing, by software or by a combination of hardware and software modules, even if the hardware is just that of a conventional computer system.

A module, and in particular the module's functionality, can be implemented in either hardware or software. In the software sense, a module is a process, program, or portion thereof, that usually performs a particular function or related functions. In the hardware sense, a module is a functional hardware unit designed for use with other components or modules. For example, a module may be implemented using discrete electronic components, or it can form a portion of an entire electronic circuit such as an application specific integrated circuit (ASIC). Numerous other possibilities exist.

FIG. 17 is a schematic representation of a computer system 400 suitable for performing the techniques described above. A computer 402 is loaded with suitable software in a memory, which software can be used to perform steps in a process that implement the techniques described herein. Programs can be executed, and results obtained using such a computer system 400. This computer software executes under a suitable operating system installed on the computer system 400.

The computer software involves a set of programmed logic instructions that are able to be interpreted by a processor, such as a CPU, for instructing the computer system 400 to perform predetermined functions specified by those instructions. The computer software can be an expression recorded in any language, code or notation, comprising a set of instructions intended to cause a compatible information processing system to perform particular functions, either directly or after conversion to another language, code or notation.

The computer software is programmed by a computer program comprising statements in an appropriate computer language. The computer program is processed using a compiler into computer software that has a binary format suitable for execution by the operating system. The computer software is programmed in a manner that involves various software components, or code means, that perform particular steps in the process of the described techniques.

The components of the computer system 400 include: the computer 402, input and output devices such as a keyboard 404, a mouse 406 and an external memory device 408 (e.g. one or more of a floppy disc drive, a CD drive, a DVD drive and a USB flash-memory drive, etc.) a display 410, network connections for connecting to a network such as the Internet 412 and/or a LAN, possibly a microarray analyzer 414 (or other mechanism for inputting gene expression data, or other data to be analyzed, standardized or otherwise processed). The computer 402 includes: a processor 422, a first memory such as a ROM 424, a second memory such as a RAM 426, a network interface 428 for connecting to external networks, an input/output (I/O) interface 430 for connecting to the input and output devices, a video interface 432 for connecting to the display, a storage device such as a hard disc 434, and a bus 436.

The processor 422 executes the operating system and the computer software executing under the operating system. The random access memory (RAM) 426, the read-only memory (ROM) 424 and the hard disc 434 are used under direction of the processor 422. The video interface 432 is connected to the display 410 and provides video signals for display on the display 410. User input, to operate the computer 402 is provided from the keyboard 404 and the mouse 406. The internal storage device is exemplified here by a hard disc 434 but can include any other suitable storage medium.

Each of the components of the computer 402 is connected to the bus 436 that includes data, address, and control buses, to allow these components to communicate with each other.

The computer system 400 can be connected to one or more other similar computers via the Internet, LANs or other networks.

The computer software program may be provided as a computer program product. During normal use, the program may be stored on the hard disc 434. However, the computer software program may be provided recorded on a portable storage medium, e.g. a CD-ROM or a flash memory read by the external memory device 408. Alternatively, the computer software can be accessed directly from the network 412. As such, the software may not even be stored on the computer itself.

In either case, a user can interact with the computer system 400 using the keyboard 404 and the mouse 406 to operate the programmed computer software executing on the computer 402. Alternatively, the process can be carried out automatically on the input of appropriate data.

The computer 400 can analyze the microarray data from microarrays directly or analyze non-standardized expression level data or standardized expression level data, as described above, to determine, represent and/or extract biclusters from such data. The means for inputting the data can be the microarray analyzer 414, the network interface 428, the external memory device, the keyboard 404 or any other suitable approach.

The computer system 400 is described for illustrative purposes: other configurations or types of computer systems can be equally well used to implement the described techniques. The foregoing is only an example of a particular type of computer system suitable for implementing the described techniques.

Other embodiments of the invention will be apparent to those skilled in the art from consideration of the specification and practice of the invention. Furthermore, certain terminology has been used for the purposes of descriptive clarity, and not to limit the present invention. The embodiments and preferred features described above should be considered exemplary, with the invention being defined by the appended claims and/or as described.

The invention claimed is:

1. A method of data mining for biclusters in data at least partially using a processor in communication with a memory storing instructions for execution by the processor to perform the method, the method comprising detecting hyperplanes in said data, said hyperplanes having at least two dimensions and obeying an equation $$F_M = \sum_{i=1}^{M-1} \beta_i F_i + \beta_M,$$

wherein $\{F_1, F_2, \ldots, F_M\}$ are co-ordinates of points in the data and $\{\beta_1, \beta_2, \ldots, \beta_M\}$ are parameters and M corresponds to a number of dimensions in the data, determining whether the hyperplanes represent biclusters in the data, and outputting the determined biclusters, wherein detecting hyperplanes in said data comprises transforming the data into parameter space by applying a transform to the data, wherein the determining comprises determining if the detected hyperplanes correspond to one or more biclusters selected from a group consisting of: constant biclusters, constant rows, constant columns, coherent values with additive model, coherent values with multiplicative model whereby each row or column can be obtained by multiplying another row or column by a constant value, and coherent values on columns with linear model whereby each column may be obtained by multiplying another column by a constant value and then adding a constant.

2. The method according to claim 1, wherein the transform comprises a Hough transform.

3. The method according to claim 2, wherein the Hough transform comprises a fast Hough transform.

4. The method according to claim 1, wherein the data comprises a set of data and further comprising, prior to detecting hyperplanes, splitting the data into a plurality of separate blocks of data and wherein detecting hyperplanes is performed separately for each of the plurality of separate blocks.

5. The method according to claim 4, wherein the data corresponds to a two-dimensional array, and wherein each block of said plurality of separate blocks extends across an entire length of the two-dimensional array in a first direction and a part of the length of the two-dimensional array in a second direction.

6. The method according to claim 4, wherein the determining is performed for each of the plurality of blocks, the method further comprising:
testing whether biclusters found in a given block extends into data in another block; and
wherein the outputting comprises outputting located biclusters for all of the plurality of blocks.

7. The method according to claim 6, further comprising, prior to outputting located biclusters, detecting and deleting duplicated biclusters.

8. The method according to claim 7, further comprising, prior to the splitting, hierarchically clustering the data.

9. The method according to claim 1, wherein the biclusters that are located include two or more biclusters that overlap in the data.

10. The method according to claim 1, wherein said data is selected from a group consisting of: gene expression data, chemical reaction data, chemical process data, electoral data, spending data and financial data.

11. The method according to claim 1, wherein said data is gene expression data derived from a plurality of microarrays.

12. The method according to claim 1, wherein said data corresponds to a two-dimensional array, with the biclusters comprising a subset of data in a first one of the two dimensions exhibiting a consistent pattern over a subset of data in a second one of the two dimensions.

13. The method according to claim 1, further comprising treating said data as geometric data prior to detecting hyperplanes.

14. A method of analyzing data for biclusters, at least partially using a processor in communication with a memory storing instructions for execution by the processor to perform the method, the method comprising:
transforming said data into parameter space by applying a transform to the data;
detecting hyperplanes having at least two dimensions and obeying an equation $$F_M = \sum_{i=1}^{M-1} \beta_i F_i + \beta_M,$$

wherein $\{F_1, F_2, \ldots, F_M\}$ are co-ordinates of points in the data and $\{\beta_1, \beta_2, \ldots, \beta_M\}$ are parameters and M corresponds to the number of dimensions in the data in said transformed data; and
determining whether the detected hyperplanes represent biclusters in the data, wherein the determining comprises determining if the detected hyperplanes correspond to one or more biclusters selected from a group consisting of: constant biclusters, constant rows, constant columns, coherent values with additive model, coherent values with multiplicative model whereby each row or column can be obtained by multiplying another row or column by a constant value, and coherent values on columns with linear model whereby each column may be obtained by multiplying another column by a constant value and then adding a constant.

15. The method according to claim 14, wherein said data is selected from a group consisting of: gene expression data, chemical reaction data, chemical process data, electoral data, spending data and financial data.

16. Apparatus for analyzing data for biclusters comprising a processor in communication with a memory storing instructions for execution by the processor to perform a method, the method comprising:
transforming said data into parameter space by applying a transform to the data;
detecting hyperplanes in said transformed data, said hyperplanes having at least two dimensions and obeying an equation $$F_M = \sum_{i=1}^{M-1} \beta_i F_i + \beta_M,$$

wherein $\{F_1, F_2, \ldots, F_M\}$ are co-ordinates of points in the data and $\{\beta_1, \beta_2, \ldots, \beta_M\}$ are parameters and M corresponds to the number of dimensions in the data; and
determining whether the detected hyperplanes represent biclusters in the data,
wherein the determining comprises determining if the detected hyperplanes correspond to one or more biclusters selected from a group consisting of: constant biclusters, constant rows, constant columns, coherent values with additive model, coherent values with multiplicative model whereby each row or column can be obtained by multiplying another row or column by a constant value, and coherent values on columns with linear model whereby each column may be obtained by multiplying another column by a constant value and then adding a constant.

17. The apparatus according to claim 16, comprising a dedicated circuit for detecting hyperplanes.

18. The apparatus according to claim 16, comprising a programmed circuit for detecting hyperplanes.

19. The apparatus according to claim 16, comprising a computer, said computer having a processor for running software to treat the input data as geometric data and detect hyperplanes in said data.

20. The apparatus according to claim 16, wherein said data is treated as geometric data.

21. A computer program product for analyzing data for biclusters, the computer program product comprising: a storage medium readable by a computer and storing instructions for execution by the computer for performing a method comprising: transforming said data into parameter space using a transform, detecting hyperplanes in said data, said hyperplanes having at least two dimensions, determining whether the detected hyperplanes represent biclusters in the data, and outputting biclusters located thereby, wherein the determining comprises determining if the detected hyperplanes correspond to one or more biclusters selected from a group consisting of: constant biclusters, constant rows, constant columns, coherent values with additive model, coherent values with multiplicative model whereby each row or column can be obtained by multiplying another row or column by a constant value, and coherent values on columns with linear model whereby each column may be obtained by multiplying another column by a constant value and then adding a constant.

22. The computer program product according to claim 21, wherein said storage medium comprises a portable memory.

23. The computer program product according to claim 21, wherein said storage medium comprises a memory, accessible for executing said instructions remotely, via a network.

24. A method of data mining for biclusters in data at least partially using a processor in communication with a memory storing instructions for execution by the processor to perform the method, the method comprising detecting hyperplanes in said data, said hyperplanes having at least two dimensions, determining whether the hyperplanes represent biclusters in the data, and outputting the determined biclusters, wherein detecting hyperplanes in said data comprises transforming the data into parameter space by applying a transform to the data; and wherein the biclusters are coherent values with additive model whereby each row or column can be obtained by adding a constant to another row or column, or coherent values with multiplicative model whereby each row or column can be obtained by multiplying another row or column by a constant value, or coherent values on columns with linear model whereby each column may be obtained by multiplying another column by a constant value and then adding a constant.

* * * * *